US012245824B2

(12) United States Patent
Higgins et al.

(10) Patent No.: US 12,245,824 B2
(45) Date of Patent: Mar. 11, 2025

(54) MULTI-DESTINATION PROCEDURE PLANNING AND GUIDANCE FOR ENDOSCOPIC SURGERY

(71) Applicant: The Penn State Research Foundation, University Park, PA (US)

(72) Inventors: William E. Higgins, State College, PA (US); Trevor Kuhlengel, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 18/838,873

(22) PCT Filed: Jan. 25, 2023

(86) PCT No.: PCT/US2023/011527
§ 371 (c)(1),
(2) Date: Aug. 15, 2024

(87) PCT Pub. No.: WO2023/146903
PCT Pub. Date: Aug. 3, 2023

(65) Prior Publication Data
US 2025/0017661 A1 Jan. 16, 2025

Related U.S. Application Data

(60) Provisional application No. 63/358,935, filed on Jul. 7, 2022, provisional application No. 63/303,712, filed on Jan. 27, 2022.

(51) Int. Cl.
*A61B 34/10* (2016.01)
*A61B 1/00* (2006.01)
(Continued)

(52) U.S. Cl.
CPC .......... *A61B 34/10* (2016.02); *A61B 1/00009* (2013.01); *A61B 1/00045* (2013.01);
(Continued)

(58) Field of Classification Search
CPC . A61B 34/10; A61B 1/00009; A61B 1/00045; A61B 1/04; A61B 2034/107; G16H 20/40
See application file for complete search history.

(56) References Cited

U.S. PATENT DOCUMENTS

2008/0207997 A1  8/2008  Higgins et al.
2010/0185156 A1  7/2010  Kanner et al.
(Continued)

OTHER PUBLICATIONS

Goyette, Brina E., and Cameron N. Riviere. "Reducing operating time of a crawling robot for epicardial surgery." Proceedings of the 2010 IEEE 36th Annual Northeast Bioengineering Conference (NEBEC). IEEE, 2010. (Year: 2010).*

*Primary Examiner* — Jesse P Frumkin
(74) *Attorney, Agent, or Firm* — DINSMORE & SHOHL LLP

(57) ABSTRACT

A method for planning a tour visiting a set of target diagnostic sites via endoscopy passing through a hollow organ system includes computing a 3D virtual space of the hollow organ system based on the 3D imaging scan depicting the diagnostic sites and hollow organ system, computing a series of preliminary endoscopic routes leading to each diagnostic site including a set of contiguous device poses through the hollow organ system that connect each target diagnostic site to all of the other target diagnostic sites, and computing an optimal tour having a minimum cost corresponding to the smallest set of contiguous poses that visit all of the target diagnostic sites once and only once, where the cost between each pair of diagnostic sites is defined as the distance accumulated by the smallest set of contiguous poses
(Continued)

connecting the pair of diagnostic sites together within the hollow organ system.

12 Claims, 16 Drawing Sheets

(51) Int. Cl.
 *A61B 1/04* (2006.01)
 *G16H 20/40* (2018.01)
(52) U.S. Cl.
 CPC ............... *A61B 1/04* (2013.01); *G16H 20/40* (2018.01); *A61B 2034/107* (2016.02)

(56) References Cited

U.S. PATENT DOCUMENTS

| | | |
|---|---|---|
| 2011/0275891 A1 | 11/2011 | Shemi |
| 2015/0257847 A1 | 9/2015 | Higgins et al. |
| 2021/0378644 A1* | 12/2021 | Stoianovici ............ A61B 8/085 |
| 2021/0386491 A1 | 12/2021 | Shmayahu et al. |

* cited by examiner

FIG. 1
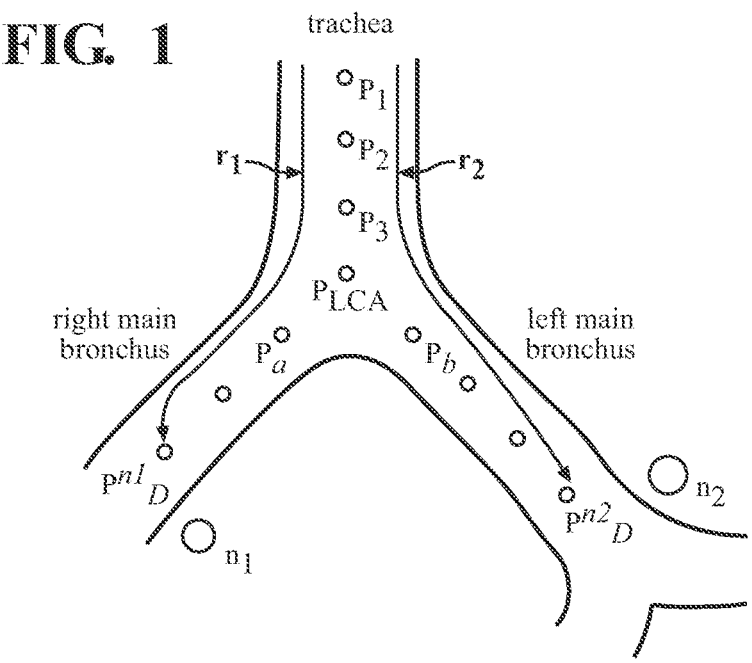
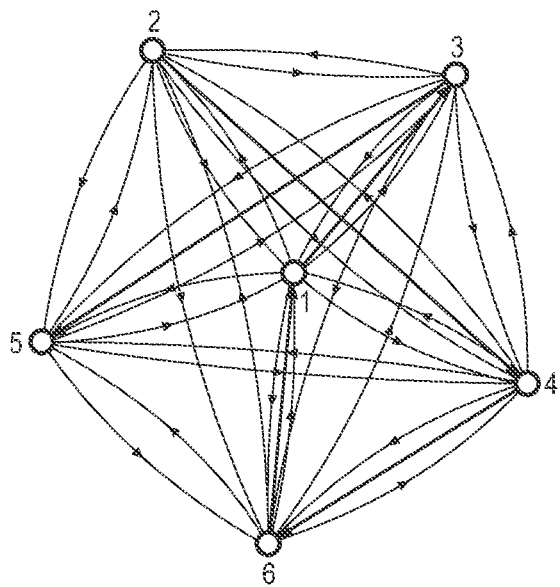
FIG. 2A
FIG. 2B
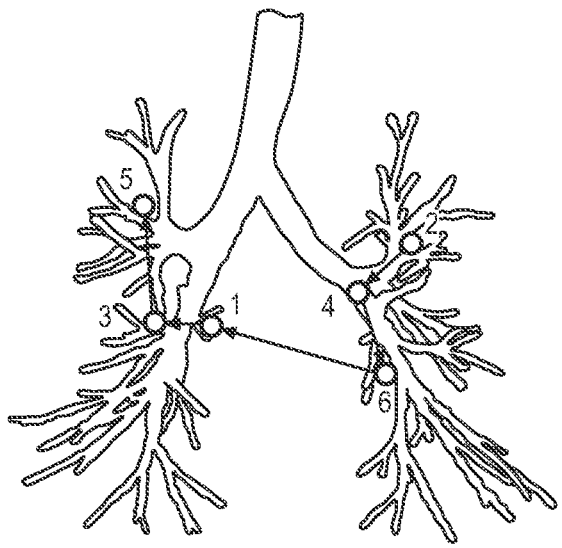

3D Airway Tree

FIG. 12A
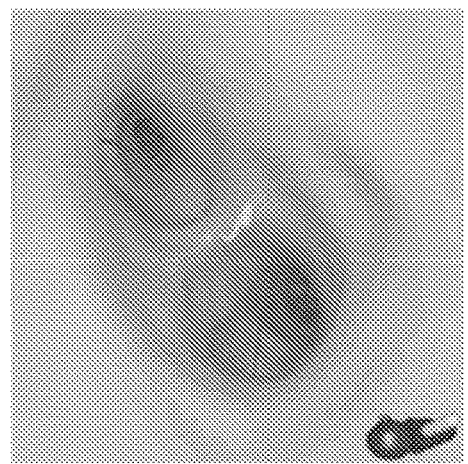
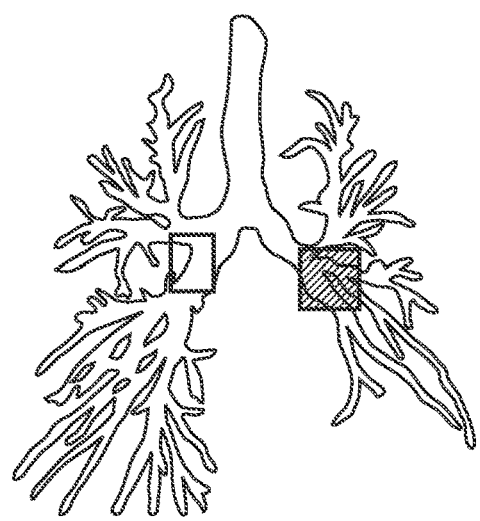
FIG. 12B
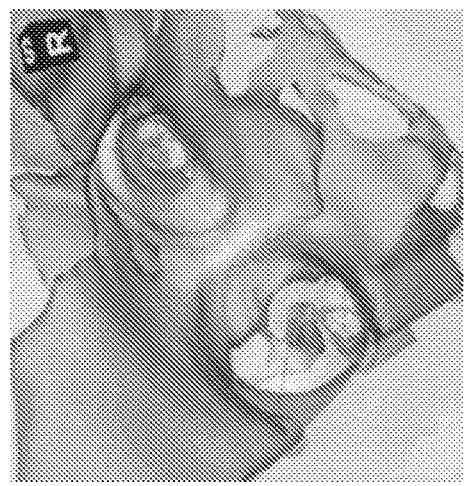
FIG. 12C

FIG. 12D
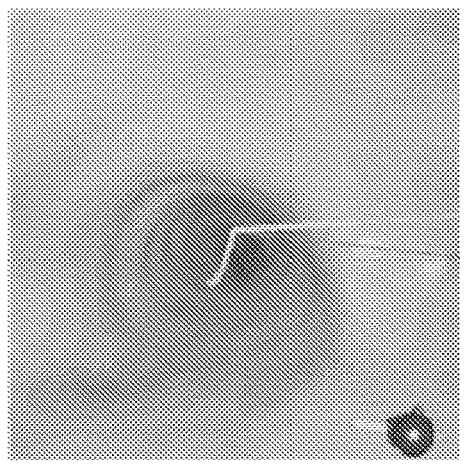
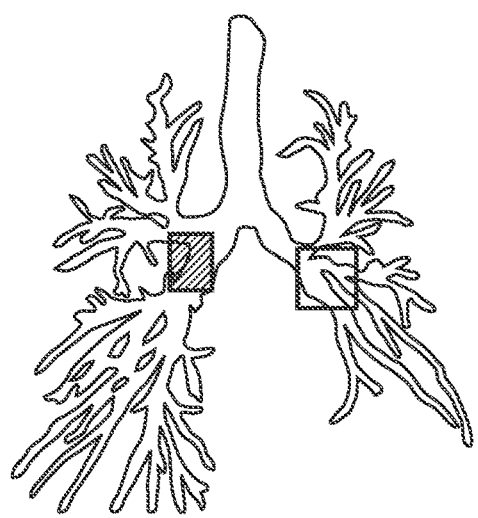
FIG. 12E
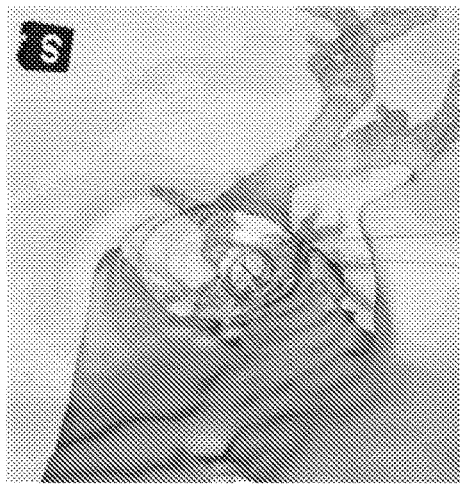
FIG. 12F

FIG. 12G
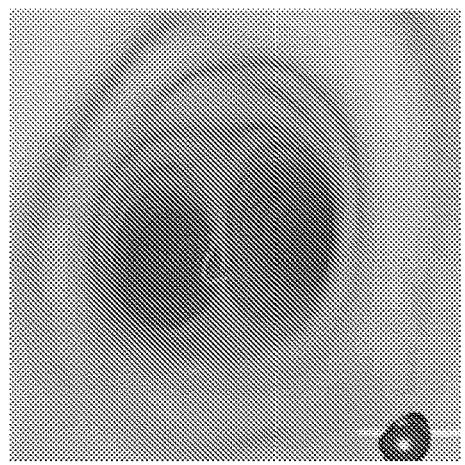
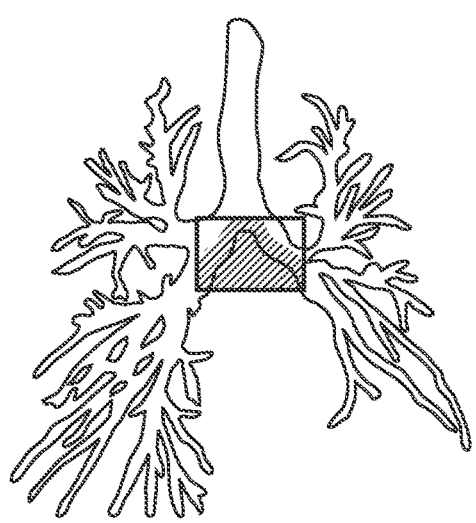
FIG. 12H
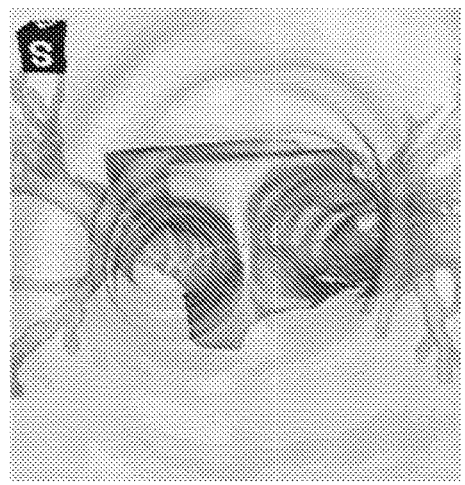
FIG. 12I

| | Name | Confirm | Color | Station | Staging |
|---|---|---|---|---|---|
| 1 | ROI 9 | ☐ | ☐ | 12R | N3 |
| 2 | ROI 11 | ☐ | ☐ | 10R | N2 |
| 3 | ROI 17 | ☐ | ☐ | 10R | N3 |
| 4 | ROI 3 | ☐ | ☐ | 4R | N3 |
| 5 | ROI 14 | ☐ | ☐ | 4L | N2 |
| 6 | ROI 18 | ☐ | ☐ | 10L | N1 |

LNS Procedure Order Tool — Master | Stations | Options
M7, 10L, 10R, LUL, RUL, LLL

MULTI-DESTINATION PROCEDURE PLANNING AND GUIDANCE FOR ENDOSCOPIC SURGERY

CROSS-REFERENCE TO RELATED APPLICATIONS

This application is the U.S. National Stage of PCT/US2023/011527 filed on Jan. 25, 2023, which claims priority from U.S. Provisional Patent Application Ser. No. 63/303,712, filed on Jan. 27, 2022, and U.S. Provisional Patent Application Ser. No. 63/358,935, filed Jul. 7, 2022 the entire content of both are incorporated herein by reference in their entirety.

GOVERNMENT SPONSORSHIP

This invention was made with government support under Grant No. CA151433 awarded by the National Institutes of Health. The Government has certain rights in the invention.

FIELD OF THE INVENTION

This invention relates generally to surgical procedure planning and guidance and, in particular, to a multi-destination route planning method and guidance methodology, applicable to guided endoscopy and other fields.

BACKGROUND OF THE INVENTION

Many surgical applications, especially those that entail traversing hollow tubular anatomical structures using an endoscope, such as the airways, or hollow regions, such as the stomach, demand the comprehensive examination, biopsy, diagnosis, or treatment of multiple distributed sites across an anatomical region. Examples of such applications are discussed in the literature [17, 20, 23, 27, 37, 55, 56, 61, 63] and include:
  1. The staging of the lymph nodes within the chest.
  2. Examination of the airways spanning the two lungs for the purpose of treatment delivery for asthma, cancer, and other diseases.
  3. Repeat airway exams of the two lungs for disease monitoring and follow-up over exams done at different times (e.g., monitoring lung tumor development or transplant rejection).
  4. Guidance to multiple mucosal (airway wall) lesions within the chest. Such lesions could be early indicators (biomarkers) of cancer formation or genesis.
  5. Examination of the vasculature within an organ for the purpose of locating narrowed vessels (stenoses). Organs such as the heart, brain, liver, and kidney have extensive vascular networks. A diseased (stenosed) vessel could indicate a high risk for heart attack or stroke, for example.
  6. Examining and biopsying multiple suspect cancerous polyps within the colon.
  7. Using laparoscopy within the abdomen, stomach, or pelvic region to examine and or treat multiple diagnostic sites.

Such comprehensive procedures—i.e., those that entail a large number of surgical sites ("destinations") to perform satisfactorily—currently are never done, because they are too complex or impractical. Two issues cause this state of affairs. First, physician skill variations result in a wide range of performance for various procedures. Second, the requisite tools do not exist to efficiently plan and then later complete such a procedure. In addition, while a human would likely always have considerable difficulty performing such a procedure in even the best of circumstances, a suitable automated robot would likely be able to perform such a procedure far more efficiently without any dependence on physician skill. Unfortunately, even for robotics applications, no means currently exist for planning and guiding such complex procedures.

Focusing on a particular field, lung cancer is responsible for over 20% of all cancer-related deaths in the United States [62]. For a patient at risk of having lung cancer, the physician diagnoses and stages the disease in two steps [56, 63]. First, drawing upon the patient's chest computed-tomography (CT) imaging scan and, if available, positron emission tomography (PET) scan, the physician plans the procedure off-line by identifying a suspect metastatic lung tumor and any suspicious chest lymph nodes. Next, during surgery, the physician uses the imaging observations to guide a bronchoscope through the lung airways to biopsy the tumor and selected lymph nodes [20]. The tumor biopsy helps confirm disease diagnosis, while the lymph node biopsies establish disease stage, or spread of the disease.

Note that accurate disease stage is vital, since it dictates follow-on treatment options and disease prognosis [56, 63]. For example, a stage 1A1 patient has a five-year survival rate of 92%, while a stage IIIB patient has only a 26% rate [8]. Thus, an incomplete or inconclusive lymph node staging procedure could result in an insufficient treatment plan and have a devastating impact on the patient's survival. Unfortunately, physicians are generally unable to plan and perform sufficiently complete nodal staging procedures to ensure accurate disease staging [49, 70].

Unfortunately, lung cancer's high mortality rate persists because a high percentage of patients tend to be diagnosed with advanced stage 3-4 disease [19]. To address this problem, the current worldwide effort to roll out CT-based lung cancer screening programs is driving a major shift toward detecting early-stage treatable disease [52, 65]. This exciting development, however, greatly increases the demand for accurate staging of the chest lymph nodes [56, 63]. Unfortunately, Miller et al. found that many physicians were unlikely to perform appropriate nodal staging [49].

As a standard aid for assigning disease stage, the International Association for the Study of Lung Cancer (IASLC) has devised the TNM lung cancer staging system [8, 26, 60]. Using the TNM system, the physician derives a "Tx Ny Mz" disease class to ascertain disease stage, where the T, N, and M descriptors refer respectively to the primary Tumor, lymph Node involvement, and distant Metastases outside the thoracic cavity. The "x", "y", and "z" sub-descriptors help stratify disease spread within the three anatomical compartments. The TNM system partitions the thoracic cavity into a set of distinct nodal stations, as given by the IASLC lymph node map [8, 15]. The nodal stations are in turn assigned to staging zones N1 through N3, with the detection of a positive metastatic lymph node in a higher-numbered zone implying a more advanced disease stage [56, 60].

Current clinical guidelines recommend at least a complete sampling of the visible lymph nodes (≥6 stations considered) to accurately ascertain disease stage [9, 20, 34, 63]. This recommended staging strategy entails examining lymph nodes in the highest N3 level nodal stations first, followed by nodes in N2 level stations, and, lastly, the N1 level, with the positive node in the highest staging zone determining descriptor "Ny" [26, 34].

Unfortunately, studies have shown that most staging procedures are inadequate, with physicians generally resorting to so-called "selective sampling" of obvious nodes in a few stations or even just a single enlarged node [9, 20, 34, 38, 49]. (Zhong et al. conjectured that ≥11-16 nodes must be examined to reach a conclusive staging evaluation [70].) To this point, the physicians who participated in the large multi-center staging study of Ost et al. biopsied only 2.18 lymph nodes on average per patient, with 66% of the patients having only 1-2 nodal stations sampled [54]. Thus, lung cancer's mortality rate remains very high, because a high percentage of patients tend to be diagnosed with advanced stage 3-4 disease [19].

Physician skill limitations are a major reason for this state of affairs. Regarding these limitations, the physician must first review a patient's three-dimensional (3D) CT imaging scan to plan airway routes through the lungs leading to each identified diagnostic site and to decide on a lymph node sampling order [10, 51]. Next, in the surgical suite, the physician is forced to mentally translate the derived plan to live airway observations seen during bronchoscopy. Unfortunately, physicians vary greatly in their ability to construct airway routes from CT viewing and in their skill in performing bronchoscopy [10, 47, 50]. While physicians do undergo bronchoscopy training, these programs hinge on performing a minimum number of procedures instead of gaining proficiency in the necessary technical skills [16, 20, 21, 34].

Apart from this, researchers have also recognized two added burdens placed on physicians if they must perform complete nodal staging [9]. First, they are compelled to navigate the bronchoscope to many widely spaced nodal stations within the thoracic cavity. Second, they must have the skill to mentally translate the IASLC node map from 3D CT observations to live bronchoscopy. The desired procedure plan consists of an efficient "tour" through the airways of all designated lymph nodes, visited in an order conforming to clinical staging guidelines.

The task of deriving this efficient tour is an example of the Traveling Salesman Problem [31]. The traveling salesman problem is known to be NP-hard; i.e., the best algorithms that guarantee an optimal solution to the graph search formulated above have exponential-time worst-case complexity [22, 31]. As this is not feasible in practice, we need a method that can quickly find a near-optimal solution. Methods, such as nearest-neighbor search [59], local graph search heuristics [7, 40], greedy search [3], and genetic and evolutionary algorithms [39, 66] have been applied to this problem. They vary in their levels of success, with a few methods susceptible to local minima or low-quality results.

While common in industrial applications, the traveling salesman problem has seen minimal application to biomedicine, such as in the study of biological organisms [58] and surgical tool selection [53]. For surgical procedures, Goyette and Riviere applied linear optimization to minimize the travel time of a surgical robot to points on the heart's pericardial surface [27]. Madeira et al. optimized a finite element model to correct scoliosis of the spine [45]. Falcone et al. simulated a task related to laparoscopic surgery [17]. Burrows et al. simulated needle steering to enable the biopsy of several locations through one incision [4]. On a related note, Gayle et al. rigorously formulated the path planning task for guiding a flexible robot through the liver's complex vasculature, but did not consider the need for visiting multiple destinations [23]. Notably, these works generally did not use real data and none were directly applied to image-guided surgery or bronchoscopy.

On another front, for the allied lung cancer management task of peripheral tumor biopsy, recently introduced image-guided bronchoscopy systems have greatly eased a few of the aforementioned bronchoscopy skill issues [5, 6]. In particular, they use computer-based image analysis to derive an optimal airway route leading to the tumor of interest and provide live image guidance along the derived route during bronchoscopy [2, 24, 57]. As a result, these systems have proven to virtually eliminate physician-skill differences in planning and performing bronchoscopy for peripheral tumor biopsy while also improving biopsy success rate [1, 24, 47].

Regrettably, these systems only give separate distinct airway routes for each diagnostic site and offer no coordinated guidance for multiple sites. To this point, they do not provide the means for accurate comprehensive nodal staging per recommended clinical guidelines, such as: 1) a single coordinated tour for all desired lymph nodes and stations; 2) translation of the IASLC lymph node map from CT to procedure plan, thereby enabling node ordering by staging zone.

In summary, comprehensive endoscopic/surgical procedures that entail traversing complex hollow tubular anatomical regions or hollow regions in general, as required for many vital medical tasks, are not currently performed, as they are too complicated or impractical. While procedure plans can be produced for individual diagnostic sites, no means exists for efficiently planning a comprehensive procedure entailing many distributed diagnostic sites ("destinations"). In addition, no means exists for then using the created multi-destination procedure plans ("tours") for follow-on live procedure guidance.

SUMMARY OF THE INVENTION

The embodiments of the present invention provide a method for planning and guiding complex multi-destination surgical procedures that entail traversing a complex, branching, hollow, tubular organ system or other hollow organ such as abdomen, stomach etc. using an endoscope operated by an operator such as a physician. In particular, such procedures require the physician to examine, diagnose, biopsy, or treat multiple distributed sites at target region of interests across an anatomical region.

First, a 3D radiologic imaging scan of a patient's hollow organ system will be provided first and serve as a primary input. The regions of interest will be identified and a 3D virtual space of the hollow organ system can be derived from the 3D pre-operative imaging scan. The 3D imaging scan may be a CT scan or a MRI scan.

The hollow organ system may be lung airways, vasculature in a heart, brain, liver, kidney or hollow areas in a colon, stomach, bladder, or pelvis/abdomen. The endoscope may be a bronchoscope, colonoscope, laparascope, angioscope, or cystoscope. The target diagnostic sites may be lymph nodes, suspect lesions, or treatment delivery sites.

For example, drawing on a patient's 3D image scan, the method derives a patient-specific multi-destination tour for efficient navigation to all preselected lymph nodes. A route may include a set of endoscopic device poses spanning at least a portion of the hollow organ system between a pair of lymph nodes or target diagnostic site. Each pose consists of its coordinates in the 3D virtual space and a set of vectors indicating a direction of travel through the hollow organ system. Furthermore, each lymph node, or target diagnostic site, is connected to each of the other lymph nodes by a smallest subset of contiguous poses, signifying the minimum distance route between the pair of lymph nodes. The poses connect all of the lymph nodes or target diagnostic sites together. A complete set of contiguous poses visiting all of the lymph nodes or target diagnostic sites constitutes a tour. A tour constitutes routes that connects all the preselected lymph nodes or diagnostic sites together such that each and every site is visited once and only once. An optimal tour is defined as the shortest route corresponding to a minimum cost for visiting all of the lymph nodes or target diagnostic sites once and only once, where the cost indicates the distance traveled by the endoscope connecting the subset of contiguous poses together between each pair of the lymph nodes or diagnostic sites. A minimum cost is defined as the distance traveled connecting the smallest subset of contiguous poses between each pair of the lymph nodes or diagnostic sites. An optimal tour corresponds to the minimum cost tour, which is the smallest set of contiguous poses connecting all of the preselected lymph nodes or diagnostic sites together.

If each one of the diagnostic sites is considered a vertex and a distance connecting each of two vertices is considered an edge, a graph structure can be constructed. The graph structure includes a cost matrix where each cost entry implies the distance travelled to go from one target diagnostic site to another. The optimal tour is the minimum cost sequence of vertices that visits each and every vertex once and only once.

In the case of the target diagnostic sites being lymph nodes, the lymph nodes belong to certain (IASLC) anatomical nodal stations and abide IASLC guidelines. The labeled nodes are mapped to staging zones, given a known cancer nodule location. The present method further incorporates constraints imposed by the staging zones while computing the shortest route. The method determines the optimal, or near optimal, tour for visiting all target lymph nodes consistent with recommended guidelines for comprehensive lymph node staging.

To compute the desired route, the present method entails three major steps:
1. Image Scan Preprocessing: to define the target diagnostic sites and 3D model of the hollow organ system (e.g., lymph nodes, tumor, airway-tree structure, preliminary single-node airway routes, and IASLC lymph node stations).
2. Graph and Staging Zone Construction: to set up the necessary data structures for route computation.
3. Route Computation, to compute the shortest route for subsequent image-guided endoscopic examination.

A procedure plan can be devised based on the shortest route for guidance for subsequent live procedure.

Next, an image-based methodology uses the precedure plan for guiding a comprehensive, multi-destination medical procedure.

A series of graphical tools are provided including visual cues and guidance instructions. For example, planning data derived in the 3D virtual space will be linked to the real space of the live medical procedure by linking virtual endoscopy endoluminal views derived in the 3D virtual space to the live videoendoscope views of the hollow organ system within a real space of the live medical procedure.

A guidance control strategy efficiently leads the physician or surgical robot to each surgical site. For example, suggested devices maneuvers are provided for reaching each diagnostic site.

During the guided procedure, a procedure history keeps track of all guidance and imaging information of the visited sites. For each site, the path history records when the site was visited, the state of the guidance system, and the site's imaging characteristics. The procedure history records which sites have been visited and which sites are yet to be visited during the live medical procedure. The procedure history can be recalled during follow-up procedures to enable assessment of treatment or disease progress at previously examined sites.

Both the planning and guidance methodologies have been implemented as interactive software systems. The planning system accepts the appropriate radiologic imaging data and outputs a procedure plan consisting of the tour and other information to reach each surgical site optimally. The guidance system accepts the procedure plan as input and interfaces the surgical endoscopy hardware to accept live endoscopic information.

BRIEF DESCRIPTION OF THE DRAWINGS

FIG. 1 shows a schematic depiction of airway distance calculations; (Routes $r_1$ and $r_2$ for lymph nodes $n_1$ and $n_2$, respectively, shares poses $p_1$ through $p_{LCA}$ within the trachea. The two routes diverge onto different paths at poses $p_a$ and $p_b$);

FIG. 2A shows a schematic 6-node example of a graph structure and optimal tour; (CT scan from human case 21405-3a is used. FIG. 2A shows a graph structure, with nodes represented as numbered circles and edges represented as red lines;

FIG. 2B shows a CT-based airway tree rendering depicting the physical locations of the nodes and the optimal tour, shown as a series of directed black arrows; (The tour is also traced as a series of black arrows on the graph);

(FIG. 3A shows a CT-based airway tree depicting the derived tour;

(FIG. 7A shows a dynamic visualization through the airway tree that can be played as an interactive movie;

FIGS. 12A-12I show examples of the automatic nodal station views showing the automated view sites; (FIG. 12A-12C display station M10L using VB views. FIG. 12D-12F display station M10R using VB views. FIG. 12G-12I display station M7 using VB views. FIGS. 12A, 12D, 12G display endoluminal renderings using a VB camera positioned inside the airway lumen at the canonical station view location. FIGS. 12B, 12E, 12H display exterior views of the airway 3D surface, displaying the soft tissue surface of the lymph node station inside the station cuboid (red) and an airway guidance route to the location (blue). FIG. 12C, 12F, 12I display translucent endoluminal renderings, which use the same camera pose as the left column to show through the airway wall, reveal the surfaces of the soft tissue volume from inside the airway. (Data from case 21405-67));

DETAILED DESCRIPTION OF THE INVENTION

Figure 3A:
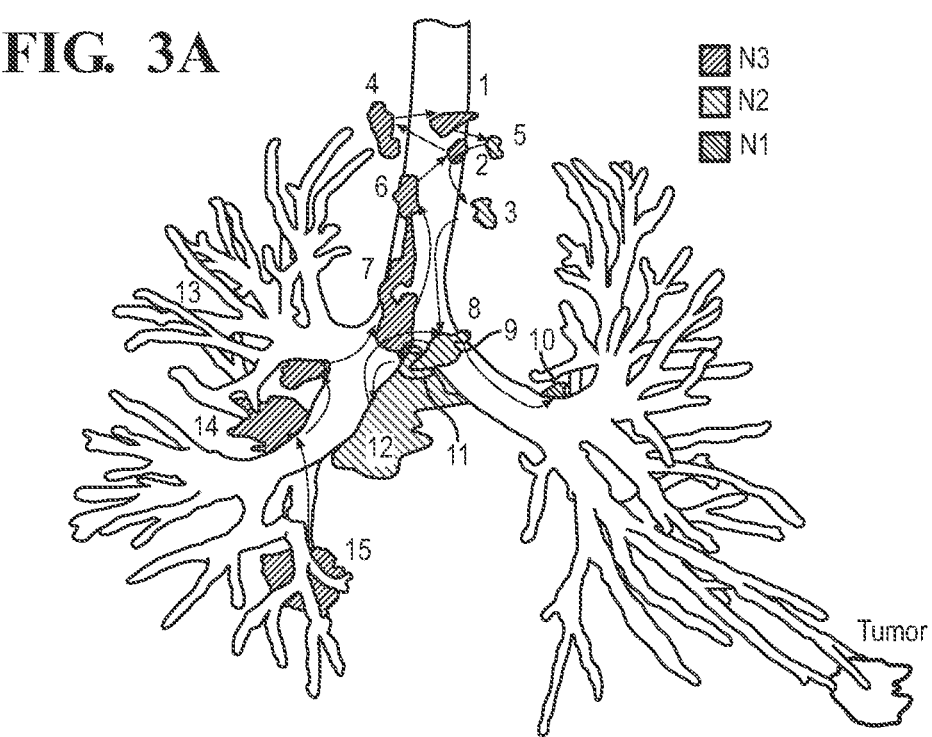
FIG. 3A shows a complete example for human case 20349-33.

The present invention provide a method and a system for planning and guiding complex multi-destination surgical procedures that entail navigating a hollow organ system using an endoscope operated by an operator such as a physician or a surgical robot. In particular, such procedures require the physician to examine, diagnose, biopsy, or treat multiple destination sites at target regions of interest.

A 3D imaging scan of a patient's hollow organ system will be provided and serve as a primary input. The regions of interest will be identified and a 3D virtual space of the hollow organ system can be derived from the 3D pre-operative imaging scan.

Drawing on the patient's 3D image scan, the present method derives a patient-specific multi-destination route for efficient navigation to all preidentified lymph nodes. A route may include a set of endoscopic device poses spanning at least a portion of the hollow organ system between a pair of lymph nodes or target diagnostic site. Each pose consists of its coordinates in the 3D virtual space and a set of vectors indicating a direction of travel through the hollow organ system.

A complete set of contiguous poses visiting all of the lymph nodes or target diagnostic sites constitutes a tour. An optimal tour is defined as the shortest route corresponding to a minimum cost for visiting all of the lymph nodes or target diagnostic sites once and only once, where the cost indicates the distance traveled by the endoscope connecting the subset of contiguous poses between each pair of the lymph nodes or diagnostic sites. A minimum cost is defined as the distance traveled connecting the smallest subset of contiguous poses between each pair of the lymph nodes or diagnostic sites. An optimal tour corresponds to the minimum cost tour, which is the smallest set of contiguous poses connecting all of the preselected lymph nodes or diagnostic sites together.

A procedure plan can be devised based on the shortest tour for guiding the subsequent live procedure.

Next, an image-based methodology uses the precedure plan for guiding a comprehensive, multi-destination medical procedure.

Returning to the lung cancer problem, the desired comprehensive nodal staging plan, or tour, is a continuous path through the airways over a set of designated lymph nodes visited in an order conforming to clinical staging guidelines. For the colon cancer diagnosis, the plan would be a continuous path through the colon touring various suspect cancerous polyps. To find the appropriate tour, the problem is cast into a form of the Traveling Salesman Problem, which can be stated as follows [31]. A salesman wishes to visit N interconnected cities in his/her sales territory once and only once. Because travel is expensive, the salesman wants the shortest tour connecting these cities.

For nodal staging, the territory corresponds to the lung airways, and the cities are the lymph nodes $$n_i, i=1,2,\ldots,N. \tag{1}$$

In general, for $$N \geq 3, \frac{N!}{2}$$

tours are possible [39]. Thus, for N=3 lymph nodes, only three tours exist:

$$n_1 \to n_2 \to n_3, n_1 \to n_3 \to n_2, \text{ and } n_3 \to n_1 \to n_2.$$

(Note that tour $n_3 \to n_2 \to n_1$ is equivalent to $n_1 \to n_2 \to n_3$, etc.) Unfortunately, as N increases, a brute-force search through all possible tours becomes impractical. For example, for a patient with N=23 identified lymph nodes, an astronomical $1.293 \times 10^{22}$ tours are possible.

To find the shortest tour, the problem is formulated as an optimal graph search, where the search space is defined by a directed graph consisting of:

A set of vertices $$V=\{1,2,\ldots,N\} \tag{2}$$

where each vertex $i=1,2,\ldots,N$, represents a lymph node $n_i$ in set (1).

A set of edges $$E=\{(i,j), i,j \in V\} \tag{3}$$

connecting each pair of vertices (i,j), or, equivalently, each lymph node pair $(n_i, n_j)$, where the airway tree defines the physical space delineating all possible connections.

An N×N cost matrix $$C(i,j)=c_{ij}, i,j=1,2,\ldots,N, \tag{4}$$

where $c_{ij} \geq 0$ is the cost associated with each edge (i,j). For our problem, $c_{ij}$ will equal the airway distance between nodes $n_i$ and $n_j$.

The desired tour is the minimum cost sequence of vertices (lymph nodes) that visits each and every vertex once and only once.

The present method for planning a comprehensive nodal staging procedure incorporates these features. In particular, drawing on a patient's chest CT scan, the method derives a patient-specific multi-destination tour for efficient navigation to all preselected lymph nodes. The planning task is formulated as a traveling salesman problem per the graph search problem defined by (1-4). To solve this problem, the concept of ant colony optimization (ACO) is applied to derive an airway tour connecting the target lymph nodes [11-14]. ACO is an iterative algorithm featuring a random element, whereby a colony of "worker ants" create separate tours through the graph. After each iteration, the most frequently visited tour edges get "pheromone" deposits that increase their attractiveness (likelihood) to the ants for tours in future iterations. As discussed later, ACO is chosen because it consistently derives optimal or near optimal tours in polynomial-time complexity [64, 71].

In addition, our method further constrains the optimization by incorporating CT-derived nodal station labels, primary tumor location, and staging zones. Thus, the method determines the optimal, or near optimal, shortest tour for visiting all target lymph nodes consistent with recommended guidelines for comprehensive lymph node staging.

Consider the complete nodal staging task for a patient involving N pre-identified lymph nodes (1) and a primary tumor. The goal is to compute the shortest-distance tour through the airway tree such that all lymph nodes are visited once, while abiding by current lung cancer staging guidelines.

The patient's 3D pre-operative chest CT scan serves as the primary input and delineates the discrete 3D chest space used for all computations. As with modem image-guided bronchoscopy systems, high-resolution scans are used [33, 42, 57]. In particular, we draw on scans having axial-plane resolution $\Delta x$, $\Delta y < 1.0$ mm and section spacing $\Delta z = 0.5$ mm. Such scans afford sub-millimeter accuracy for airway distance calculations, and they enable detailed definition of the airways, which have endoluminal diameters ranging from 3.5 mm to 20 mm [24], and clinically relevant lymph nodes, which have short-axis diameters $\geq 10$ mm [56].

To compute the desired tour, the present method entails three major steps:

1. CT Preprocessing, to define the lymph nodes, tumor, airway-tree structure, preliminary single-node airway routes, and IASLC lymph node stations.
2. Graph and Staging Zone Construction, to set up the necessary data structures for tour computation.
3. Tour Computation, to arrive at the nodal staging plan for subsequent image-guided bronchoscopic nodal staging.

The tour then gives a procedure plan for subsequent live guidance.

Next, an image-based methodology for guiding a comprehensive, multi-destination lymph node staging procedure is applied for live bronchoscopy guidance. Drawing on the procedure plan, the methodology incorporates: 1) a series of graphical tools that provide visual cues and guidance instructions; 2) a guidance control strategy that efficiently leads the physician or surgical robot to each surgical site; and 3) a procedure history mechanism that records all guidance and imaging information related to examined sites. Both the planning and guidance methodologies have been implemented as interactive software systems. The planning system accepts the appropriate radiologic imaging data and outputs a procedure plan consisting of the tour and other information to reach each surgical site optimally. The guidance system accepts the procedure plan as input and interfaces the surgical endoscopy hardware to accept live endoscopic information.

Sections 1-4 provide details and validation results for the 3-step planning method, and Section 5 provides the guidance strategy and software systems.

1. CT Preprocessing

Given the patient's chest CT scan, CT Preprocessing derives various anatomical structures necessary for follow-on operations. These include the lymph nodes, primary tumor, the airway tree structure, preliminary routes leading to each lymph node, and the IASLC lymph node stations.

To begin, 3D regions $$R_i, i=1,2,\ldots,N, \quad (5)$$

constituting each lymph node $n_i$ of set (1), along with the primary tumor, are defined. For our tests, we use the semi-automatic live wire to define these regions in the chest CT scan.

Continuing, previously devised automatic CT-analysis methods segment the airway tree and its associated airway endoluminal surfaces [25, 28]. Based on these data structures, the airway tree centerlines spanning the segmented airways are then defined, where the centerlines are modeled as a set P of bronchoscopic device poses, or view sites, given by $$P = \{p_1, p_2, \ldots, p_L\}, \quad (6)$$

where the constituent poses $p_k$ are equally spaced 0.5 mm apart [24, 25, 68, 69]. Each pose consists of its (x,y,z) location in 3D chest space and a set of vectors indicating direction of travel through the airways [24]. We only require the location for our work here. Note that the centerlines consist of a hierarchically connected set of airway branches that span the two lungs. The tree starts with the trachea and then bifurcates into two child branches (left main bronchus and right main bronchus), which in turn continue bifurcating into other constituent child branches. Each branch in turn is made up of poses from set (6). Also with (6), a path connecting two airway tree poses, $p_a$ and $p_b$, consisting of an ordered sequence of poses $$p_a, p_{a+1}, p_{a+2}, \ldots, p_b \quad (7)$$

in P can be formed, where $p_a$ is adjacent to $p_{a+1}$, $p_{a+1}$ is adjacent to $p_{a+2}$, etc.

Next, a series of separate preliminary bronchoscope airway routes leading to each lymph node is computed. These routes serve as the basis for computing the distances $c_{ij}$ required later by cost matrix C(i,j) in (4). Because the bronchoscope navigates inside the airway tree, the standard way to represent a bronchoscope's trajectory toward a diagnostic site is by a route traversing a discrete connected set of device poses following the airway centerlines, as represented in the patient's chest CT scan [1, 24, 33, 42, 69]. Adopting this approach, for each lymph node $n_i$, i=1,2,...,N, we compute a route $r_i$ consisting of a sequence of contiguous device poses in P:

$$r_i = \{p_1, p_2, \ldots, p_D^{n_i}\}. \quad (8)$$

In (8), a route $r_i$ starts from the proximal (top) end of the trachea at pose $p_1$, continues onto successor poses $p_2$, $p_3$, etc., and terminates at the pose $p_D^{n_i}$ signifying when the bronchoscope reaches destination node nt. Note that all routes start at pose $p_1$, indicative of the bronchoscope's starting position in the trachea. In addition, pose $p_1$ corresponds to the root site spawning all airway centerlines traversing the airway tree.

As a final preprocessing operation, existing automatic methods define 15 disjoint IASLC nodal stations $S_c$ representing 3D tissue regions in chest space, where c is in station index set I [30, 35, 43]:

$$c \in I = \{1,2L,2R,3,4L,4R,5,6,7,8,9,10–11L,10–11R,12–14L,12–14R\} \quad (9)$$

This computation abides by IASLC guidelines, whereby certain stations are split into disjoint left- and right-chest subregions while other stations are merged [8, 15]. Thus, in (9), descriptors "L" and "R" refer to either the left or right side of the chest, respectively, and more peripheral (higher-indexed) IASLC stations are merged, such as IASLC stations 10 and 11 into a single station "10-11." Therefore, station $S_{4R}$, for example, consists of the tissue corresponding to the right side of station 4, as depicted in the chest CT, while station $S_{12-14L}$ consists of the tissue for the left side of merged stations 12 through 14.

2. Graph and Staging Zone Construction

The graph structure $\{V, E, C(\cdot,\cdot)\}$ given by (1-4) and the staging zones, which add important staging-related tour constraints, are now constructed.

The graph vertices V immediately follow from (2). Relative to 3D chest space, each vertex i actually corresponds physically to the final pose $p_D^{n_i}$ of node $n_i$'s precomputed airway route $r_i$ per (8).

Before specifying edge set E, note that the segmented CT-based airway tree delineates a closed "air" region that serves as the bronchoscope navigation domain within 3D chest space. Hence, if the bronchoscope currently resides at node $n_i$ (physically, it would be at pose $p_D^{n_i}$), it could then conceivably travel to any of the other N−1 nodes $n_j, j \neq i$, by way of a connected series of poses in set P, similar to (7). To represent these options in the graph, each vertex i has N−1 edges (i,j), i≠j, in E.

To construct cost matrix C, each entry $c_{ij}$, which signifies the airway distance from node $n_i$ to $n_j$, must be computed. These distances can be calculated using standard binary tree concepts. As depicted in FIG. 1, the distance from node $n_i$, situated at pose $p_D^{n_i}$, to $n_j$, situated at pose $p_D^{n_j}$, is given by $$c_{ij} = \text{length}(r_i) + \text{length}(r_j) - 2 \cdot d(p_1, p_{LCA}) = \quad (10)$$
$$d(p_1, p_D^{n_i}) + d(p_1, p_D^{n_j}) - 2 \cdot d(p_1, p_{LCA}),$$

where $p_{LCA}$ represents the lowest common ancestor pose constituting routes $r_i$ and $r_j$ leading to lymph nodes $n_i$ and $n_j$, respectively, and length (r) denotes the length of a route $$r = \{p_a, p_{a+1}, \ldots, p_{b-1}, p_b\} \quad (11)$$

connecting two poses $p_a, p_b \in P$. In (10), length (r) equals the distance $d(p_a, p_b)$ between poses $p_a$ and $p_b$, given by $$d(p_a, p_b) = \sum_{k=a}^{b} \|p_k - p_{k+1}\|, \quad (12)$$

where $\|\cdot\|$ is Euclidean length. Thus, using (10-12) to fill in cost matrix C of (4) gives $$C(i,j) = \begin{cases} c_{ij}, & \text{for } i \neq j \\ \infty, & \text{for } i = j \end{cases} \quad (13)$$

for i,j=1,2, ..., N, where valid costs are only assigned to edges (i,j)∈ E. Since no valid edge cycles from a vertex i back to itself, we assign $C(i,i)=\infty$. Also, note that $c_{ij}=c_{ji}$ for all i≠j.

FIG. 2 gives a simple schematic example of a graph structure $\{V, E, C(\cdot,\cdot)\}$ drawing on a real human chest CT scan. It assumes a right-side primary tumor and has 6 lymph nodes distributed across the chest as indicated. The graph has 6 vertices and 30 edges. The values in the 6×6 cost matrix C range from 1.7 mm to 348.1 mm. The optimal tour, which starts with a left-side N3 node and has length 426 mm, is given as 2→4→6→1→3→5.

Staging zones $N_k$ are next created, where each staging zone indicates the CT-based chest subspace containing lymph nodes having a particular lymph node descriptor. For example, staging zone $N_3$ encompasses that portion of chest space where N3 nodes reside. Each $N_k$ consists of a designated union of IASLC nodal stations S, and depends on the primary tumor's location. Table 1, which follows IASLC guidelines, provides the station zone definitions [26, 60]. Thus, each $N_k$ is given simply by $$N_k = U_{c \in I_k} S_c, k=1,2,3. \quad (14)$$

In (14), station index set I of (9) is partitioned into three disjoint subsets:

$$I = U_{k=1}^{3} I_k,$$

where $I_1$, $I_2$, and $I_3$ correspond to the stations containing N1, N2, and N3 nodes, respectively, per Table 1.

TABLE 1

Mapping of the IASLC nodal stations into staging zones [26, 60]. Each row represents a lymph node staging descriptor N1 through N3 for the TNM staging class. Based on the patient's primary tumor location, columns 3 and 4 of each row list the station volumes $S_c$ by indices $c \in I$ per (9) constituting each staging zone $N_k$.

| Node Descriptor | Staging Zone | Left Lung Tumor | Right Lung Tumor |
|---|---|---|---|
| N1 | $N_1$ | 10-11L, 12-14L | 10-11R, 12-14R |
| N2 | $N_2$ | 2L, 3, 4L, 5, 6, 7, 8, 9 | 2R, 4R, 3 7, 8, 9 |
| N3 | $N_3$ | 2R, 4R, 10-11R, 12-14R | 2L, 4L, 5, 6, 10-11L, 12-14L |

As a final operation, station labels $l_i$ and lymph node descriptors $z_i$ are assigned to each lymph node $n_i$, i=1,2, ..., N, as follows. First, $$l_i = \underset{c \in I}{\text{argmax}} |R_i \cap S_c|, \quad (15)$$

where $|\cdot|$ denotes set cardinality and $R_i$ is the 3D region corresponding to $n_i$ per (5). Thus, by convention, $n_i$ is assigned to the station that it most overlaps [35, 43]. Lastly, given it, descriptor $z_i$ immediately follows from Table 1. For example, if a patient exhibiting a left-lung tumor has a lymph node $n_i$ in station $l_i$=10−11R, then $l_i \in I_3$, implying that this is an N3 node with $z_i$=N3.

3. Tour Computation

To derive the desired lymph node tour, we cast the search as a variant of the traveling salesman problem over a search space defined by graph $\{V, E, C\}$. The goal is to derive an optimal tour of the form $$F = \{f_1, f_2, \ldots, f_N\} \quad (16)$$

consisting of N ordered vertices $f_p \in V$, $p=1,2,\ldots,N$, abiding by the constraint $$\forall f_p, f_q \in F, \text{ if } p \neq q, \text{ then } f_p \neq f_q \quad (17)$$

(i.e., each vertex $f_p$ is visited once and only once along the tour), such that the tour minimizes the tour length $$L(F) = \sum_{p=1}^{N-1} C(f_p, f_{p+1}) \quad (18)$$

over all possible tours F. That is, we wish to solve the optimization problem $$F_{opt} = \arg\min_F L(F) \quad (19)$$

subject to constraint (17). Note that (16-17) imply that each candidate tour F visits the following edges $(f_p, f_{p+1}) \in E$ in sequential order:

$$(f_1, f_2), (f_2, f_3), \ldots, (f_{N-1}, f_N).$$

To solve the problem posed by (16-19), we adapt a variant of ant colony optimization (ACO) [11-14]. In summary, the method goes as follows.

Over M iterations, K worker ants independently construct complete candidate tours traversing the set of vertices V. During an iteration, each ant creates a candidate tour by selecting vertices driven by a state transition rule. In general, ants are attracted to shorter edges scented by a large quantity of pheromone. The amount of pheromone at an edge (r,s) indicates its overall attractiveness to the ants for candidate tours. After all ants have constructed their tours, the lowest-cost tour $F_{best}$ having tour length $L(F_{best})$ is noted and the current optimal tour $F_{opt}$ is updated accordingly. To conclude an iteration, two update rules modify the edge pheromone amounts. First, a global update rule rewards the lowest-cost tour by adding pheromone inversely proportional to the tour's length to each edge on the tour. Next, a local update adds fixed pheromone amounts to all edges visited by any of the K ants. Both updates also include some evaporation of the pre-existing pheromone at all visited edges. The process then repeats for the next iteration, with the final $F_{opt}$ returned after iteration M.

Complete method detail appears below.

To initialize the search, two N×N matrices, which quantify the relative attractiveness of each graph edge, are set. The first of these is a fixed distance heuristic matrix Ti, which simply consists of the reciprocals of the edge costs in C per (4) and (10-13):

$$\eta(r,s) = 1/c_{r,s}, r,s = 1,2,\ldots,N. \quad (20)$$

Next, a pheromone matrix $\tau$, also referred to as an edge desirability matrix, is initialized as $$\tau(r,s) = \tau_0, r,s = 1,2,\ldots,N, \quad (21)$$

where $\tau_0 > 0$ is a parameter and element $\tau(r,s)$ denotes the amount of pheromone currently deposited on the edge connecting vertex r (node $n_r$) to vertex s (node $n_s$). For $\tau_0$, we use the widely applied suggestion [14]

$$\tau_0 = \left(\frac{1}{N}\sum_{i,j} C(i,j)\right)^{-1} \quad (22)$$

The higher an edge's pheromone amount, the more desirable it is for an ant to travel along. Thus, all edges are equally attractive to the ants at the beginning. The pheromone matrix serves as a learned component, shared by all ants and updated after every iteration. As a final initialization, the ordered vertex set and length for the desired optimal tour is initialized:

$$F_{opt} = \emptyset, L_{opt} = \infty. \quad (23)$$

Next, for each iteration $m=1,2,\ldots,M$, a candidate tour is created for each of the K ants by a probabilistically constrained random walk through the airway tree graph. For the $k^{th}$ ant, this begins by initializing its tour vertex set and length:

$$F_k = \emptyset, L(F_k) = 0.$$

Next, a vertex $r \in V$ is randomly selected to start the tour to give $$F_k = \{r\}, \quad (24)$$

where all vertices r are equally likely to be selected at the outset. The next successor vertex s is then selected via the state transition rule:

$$s = \arg\min_{u_p \in \{V/F_k\}} \{c_k(r, u_p) \geq x\}, \quad (25)$$

where operator "A/B" denotes that part of set A not in set B, set $$V/F_k = \{u_1, u_2, \ldots, u_p, \ldots\} \quad (26)$$

is the ordered set of vertices not yet on the $k^{th}$ ant's tour, x is a uniform random variable distributed over [0,1], and $$c_k(r, u_p) = \sum_{u \in \{V/F_k\}} p_k(r, u) \quad (27)$$

is a cumulative distribution function (cdf) defined in terms of the probability density function $$p_k(r, u) = \begin{cases} \dfrac{\tau(r,u) \cdot \eta(r,u)^\beta}{\sum_{u \in \{V/F_k\}} \tau(r,u) \cdot \eta(r,u)^\beta}, & \text{if } u \in V/F_k \\ 0, & \text{otherwise} \end{cases} \quad (28)$$

($\beta > 0$ is a parameter). Note that when tour $F_k$ is in state (24), $$V/F_k = \{1, 2, \ldots, r-1, r+1, \ldots, N\}.$$

In (28), $p_k(r,u)$ dictates the desirability of candidate vertices $u \in V/F_k$ and denotes the probability that ant k chooses to move from vertex r to vertex u. As (28) makes clear, $p_k(r,u)$ weighs both a candidate next edge (r,u)'s length and pheromone amount, with $\beta$ helping to regulate the relative weight. The cdf $c_k$ defined by (27) in addition to the random variable x in (25) gives an equitable means for cycling through the various candidate successor vertices during tour construction. After applying state transition rule (25), $$F_k\{r,s\}$$

and $L(F_k)$ is updated using (18). Subsequent vertices are added similarly until $V/F_k = \emptyset$, implying that tour $F_k$ is complete. Note that our implementation performs this process in parallel for all K ants.) After deriving all K tours, the tour having the shortest length is noted:

$$F_{best} = F_k, L(F_{best}) = L(F_k) \text{ such that } k = \arg\min_{k=1,2,\ldots,K} L(F_k). \quad (29)$$

If $L(F_{best}) < L_{opt}$, then $F_{opt}$ and $L_{opt}$ are updated.

To conclude an iteration, pheromone matrix $\tau$ undergoes two updates that serve to both dissipate (evaporate) and increase the pheromone amounts at certain edges based on the travel experiences obtained by the K ants. First, a global update rule rewards the best ant by depositing pheromone on all of the edges it traveled along, with the total amount of deposited pheromone inversely proportional to the length of the ant's tour; i.e., for all r, $s \in F_{best}$, $$\tau(r,s)(1-\alpha) \cdot \tau(r,s) + \alpha \cdot \Delta \tau_{global}(r,s), \quad (30)$$

where $$\Delta \tau_{global}(r,s) = 1/L(F_{best}) \quad (31)$$

Next, a local update rule adds a fixed amount of pheromone $\Delta \tau_{local}(r,s) = \tau_0$ to all edges visited by the K ants on the current iteration, with separate contributions added for every instance an ant visits a particular edge; i.e., for all edges (r,s) constituting one of the tours $F_k$, k=1,2, . . . , K, $$\tau(r,s) = (1 - \varphi \cdot \tau(r,s) + \rho \cdot \Delta \tau_{local}(r,s). \quad (32)$$

In (30) and (32), $0 \le \alpha, \rho \le 1$ are parameters and $\tau_0$ is given by (22) used to assign initial values to $\tau$ in (21). By doing these updates, variety in the choice of edges visited by the ants in future tours is encouraged.

The tour construction process above, as defined by (24-32), does not include any constraints related to the specific surgical task. For some tasks, such a tour is sufficient. For other surgical tasks that impose specialized constraints, it is a simple matter to work them into the total plan.

For example, returning to our nodal staging plan, we note that the method of (24-32) does not incorporate staging zone constraints. Hence, all remaining vertices (nodes), regardless of their assigned nodal descriptor $z_i$, are candidates to be selected as the next visited vertex by state transition rule (25-28). For a proper lymph node staging procedure, all N3 nodes should be visited first, followed in turn by N2 and N1 nodes. The staging zone constraint is easily incorporated by recasting vertex set V as an ordered collection of subsets $$V^S = \{V_3, V_2, V_1\}, \quad (33)$$

where $V_3$, $V_2$, and $V_1$ consist of the vertices corresponding to the N3, N2, and N1 nodes, respectively. Thus, by using the recast set $V^S$ of (33) in (25-28), the state transition rule selects the next vertex s by first only considering the candidate N3 vertices in set $V_3$ until $V_3/F_k = \emptyset$ before then sequentially moving on to $V_2$ and $V_1$.

After completing M iterations, the resulting optimal multi-destination tour $F_{opt}$ specifies the order for visiting the N lymph nodes. For practical bronchoscopic navigation, we also construct a continuous route $r_{opt}$ through the airway tree consisting of bronchoscope device poses, similar to (7-8). The route starts in the proximal end of the trachea at device pose $p_1$ and then in succession travels to each node's destination pose $p_D^{n_i}$. This route is trivially constructed using the centerline structure given by (6); i.e., $$r_{opt} = \{p_1, p_2, \ldots, p_D^{f_1}, p_a, p_{a+1}, \ldots, p_D^{f_2}, p_b, p_{b+1}, \ldots, p_D^{f_N}\} \quad (34)$$

where poses $p_1, p_2, \ldots, p_a, \ldots \in P$ and $f_1, f_2, \ldots, f_N \in F_{opt}$. Note that poses such as $p_a$, which connect the destination poses together, can be used more than once. Also, the typical route $r_{opt}$ prescribes that the physician first navigates the bronchoscope to the "most remote" lymph node $f_1$ relative to the primary tumor and then traces through the airway tree to reach the next lymph node, etc.

Figure 3B:
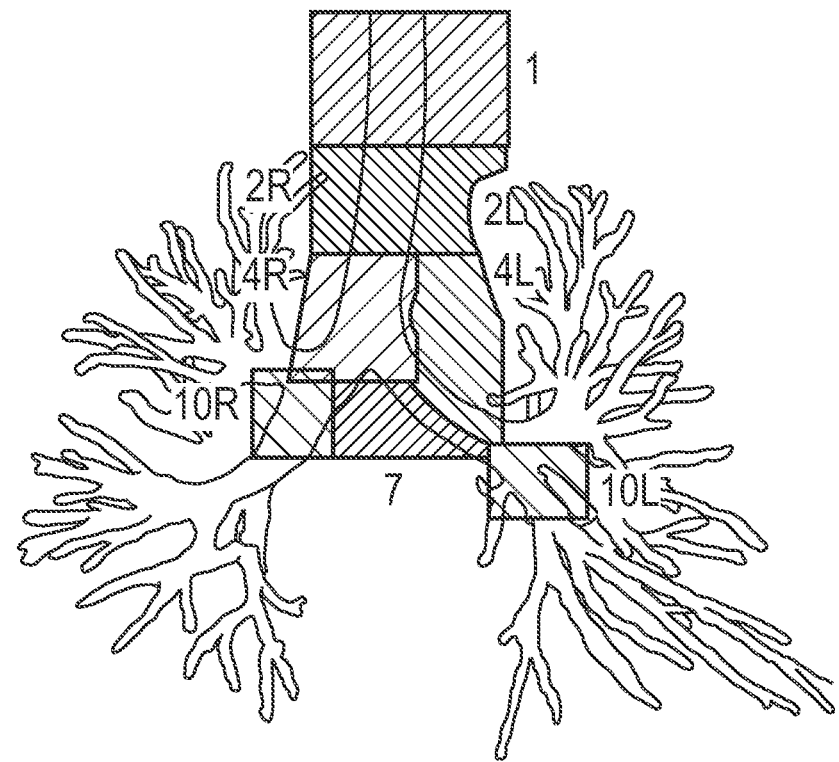
FIG. 3B shows 3D rendering of select IASLC nodal stations.
Figure 3C:
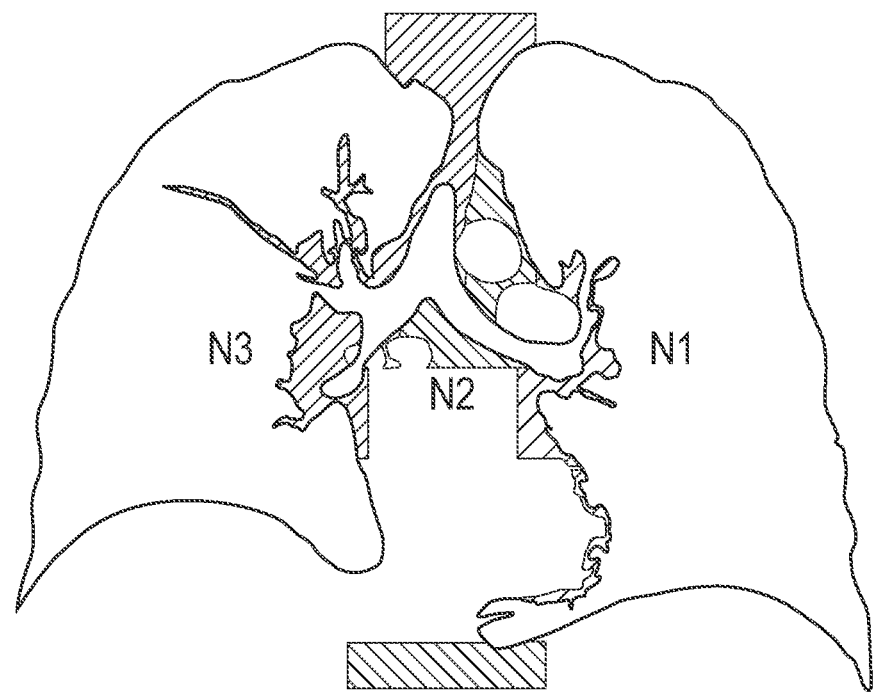
FIG. 3C shows an example 2D coronal CT section showing color-coded staging zones; (not all tissue constituting the zones is colored to help with clarity)

FIG. 3A-3D give a complete lung cancer patient example for this process. Initially, 15 lymph nodes were designated, along with a left-side tumor. Automatic computation produced the airway tree, IASLC nodal stations, and staging zones, as shown by FIGS. 3A-3C. Automatic Tour Computation then produced tour $F_{opt}$ as shown by parts a and d. This tour, having length 595 mm and computed in 248 msec, is given by $$F_{opt} = \{15, 14, 13, 7, 6, 2, 4, 1, 5, 3, 9, 11, 12, 8, 10\}$$

This tour is the true optimum for this case. Also, brute force search required 28.4 sec to produce this optimum. Notably, the graph illustrates how nodes cluster in the graph based on staging zone. The graph's bidirectional red arrows represent the edges that connect all nodes in a given staging zone, while the green arrows point in one direction from nodes in a lower staging zone to nodes in a higher zone.

Algorithms 1 and 2 give the implementation of Tour Computation. In Algorithm 1, lines 2-4 initialize the ACO algorithm, lines 5-12 derive the optimal tour, and lines 13-14 perform the updates to pheromone matrix T. At each iteration, the algorithm computes the tours for all K ants in parallel using function CreateTour (Algorithm 2). Function CreateTour cycles through (24-28) and incorporates staging zone information per (33).

---

Algorithm 1 - Ant colony optimization algorithm function ANTCOLONYSEARCH(C, $V^s$, N, I, K, $\tau_0$, β, α, ρ)
    η[r, s] ← C[r, s]$^{-1}$,    $\forall r, s \in \{1, \ldots, N\}$    // Initialize the search per (20-23)
    τ[r, s] ← $\tau_0$,    $\forall r, s \in \{1, \ldots, N\}$
    $F_{opt}$ ← { }, $L_{opt}$ ← ∞
5:  for m = 1, . . . , M do
      parallel for k = 1, . . . , K do    // Create tours for all ants in parallel
        $F_k$ = CREATETOUR(τ, η, N, β, $V^s$)
      end parallel for
      for k = 1, . . . , K do    // Update optimal tour per (29)
10:      if $L(F_k) < L_{opt}$) then
        $F_{opt}$ ← $F_k$, $L_{opt}$ = $L(F_k)$
      end for
      GLOBALUPDATE(τ, α, $F_{opt}$)    // Update τ using (30-32)
      LOCALUPDATE(τ, ρ, {$F_k$, k = 1, . . . , K})
15:  end for
    return $F_{opt}$

---

Regarding implementation of Tour Computation, we used the Eigen linear algebra library for matrix operations and OpenMP for the parallel operations of Algorithm 1 [29]. Each ant was given thread-private memory in an OpenMP thread. For Algorithm 2, line 11, we utilized a 64-bit mersenne twister to provide pseudorandom numbers for (28) [46]. Data synchronization and pheromone updates occurred at the end of each iteration.

A few points merit clarification. Each preliminary route $r_i$ in (8) actually terminates at a pose $p_D^{n_i}$ that enables maximal bronchoscopic tissue biopsy of node $n_i$. The method used to compute $r_i$ draws on the anatomical constraints depicted in the 3D chest CT scan and the specifications of the bronchoscope to be used [24, 69]. In addition, adjacent poses constituting the final tour $r_{opt}$ in (19) are spaced ≈0.5 mm apart, in line with the CT scan's spatial resolution and sufficiently spaced for later image-guided bronchoscopy.

---
Algorithm 2 - ACO tour creation for an ant
---

```
function CREATETOUR(τ, η, N, β, V^s)
    j = 3                    // Start with vertex subset V_3 per (33)
    r = GETRANDOM(V_j)
    F[1] = r                 // Assign r as the first tour vertex per
                             (24)
5:  for i = 2, ..., N do
        if V_j/F = {∅} then
            j = j - 1        // Advance search to the next staging
                             zone
        y = 0                // Apply state transition rule (25) to get
                             next vertex u
        x = UNIFORMRANDOMVALUE(0, 1)
10:     for u ∈ V_j/F, do    // Resolve (25-28)
            y = y + p_k(r, u) // p_k(r, u) given by (28)
            if y ≥ x then
                F[i] = u     // Add u as the i^th tour vertex
                break
15:     end for
        r = u
    end for
    return F
```

4. Planning Method Validation

The present methods are tested using a database of 31 lung cancer patients [44]. The patients were enrolled under informed consent at our University's hospital per IRB-approved protocol (patient age range: 28 to 85 years; 12 male, 18 female, 1 unknown). The scans were generated by either a Siemens Sensation 16, Emotion 16, or Sensation 40 multi-detector CT scanner (13 with contrast agent, 18 without). Each scan consisted of 512×512 axial-plane sections with section thickness=0.75 mm and section spacing=0.5 mm. The number of sections per scan ranged from 570 to 720, and axial-plane resolution $\Delta x = \Delta y$ ranged from 0.52 mm to 0.92 mm.

528 lymph nodes were identified in these scans (mean per scan=17; range, 3-38). These nodes were distributed over the staging zones as follows: N1, 40 nodes; N2, 312; N3, 176.

The ACO-based tour computation method is compared to four well-known algorithms: 1) exhaustive brute-force search (BFS) [31]; 2) a nearest-neighbor search (NN1) that searches one path from each possible starting node and only selects the nearest unvisited neighbor of each added node until the tour is complete [59]; 3) a K-nearest-neighbor search, with K=2 (NN2), that explores the two nearest neighbors for each node and picks the shortest overall tour that visits all nodes [32]; and a greedy "largest node first" search, which sorts nodes by physical size within each staging zone—while not an optimization algorithm per se, it is a common clinical strategy for performing nodal staging.

The tests drew on 25 of our database cases (9 male, 16 female; age range, 39 to 82 years), having a total of 403 identified lymph nodes (mean=16; range, [3,31]). The goal of all methods was to find a tour that solves optimization problem (19).

For the present method, the following default parameters were used for Tour Computation: M=1000 iterations; ant colony size K=30; weighting parameter $\beta=4.0$ in (28); best tour reward $\alpha=0.1$ in (30); pheromone evaporation rate $\rho=0.08$ in (32). The parameter choices, found via extensive training, attempt to balance the goals of deriving optimal/near-optimal tours while requiring tolerable computation time [36]. Finally, the four alternate algorithms drew on the graph and staging zones generated by CT Preprocessing and Graph/Staging-Zone Construction.

We set a threshold of 2 billion tours to explore during optimization for each case, which corresponds to a computation time≈5 min. With this constraint, brute-force search (BFS), being an NP-hard approach to the TSP, failed to reach an optimum in 9 cases when staging zone constraints were used and 16 cases when they were not. So, for these cases, we estimated a time by first computing the number of tours BFS requires for search completion and then extrapolating the time from a linear regression of the known times from other cases. The shortest estimated times for these cases were 5.28E+06 msec=88 min when using constraints (e.g., 17-node case 20349_3_13) and 205 min when not using constraints (e.g., 14-node case 20349_3_7).

Table 2 summarizes the mean computation times over the test database, while Table 3 gives example computation times for 6 cases. For all results, we tested the methods with and without staging zone constraints (33). (Table 2 excludes times for NN1 and the greedy search, as these methods gave times <1 msec for all cases. But, these methods generally give unacceptable tours.)

TABLE 2

Mean tour computation time in msec per patient case. For each column, "Mean ± std" = mean ± standard deviation, while "Range" denotes the range of times over all cases. "With Zones" uses staging zone constraints (33), while "Without" does not. ACO = ant colony optimization, NN2 = K-nearest-neighbor search with K = 2, and BFS = brute-force search. Italicized values are estimates for cases that could not reach optimum in the alloted time.

|  | With Zones | | Without | |
| --- | --- | --- | --- | --- |
|  | Mean ± std | Range | Mean ± std | Range |
| ACO | 185 ± 93 | [62, 528] | 304 ± 127 | [105, 519] |
| NN2 | 17,500 ± 65,600 | [1, 3.29E+5] | 96,800 ± 4.58E+5 | [1, 2.34E+6] |
| BFS | *4.84E+19 ± 2.40E+20* | *[1, 1.25E+21]* | *4.62E+28 ± 2.23E+29* | *[3, 1.16E+30]* |

Table 2: Mean tour computation time in msec per patient case. For each column, "Mean±std"=mean±standard deviation, while "Range" denotes the range of times over all cases. "With Zones" uses staging zone constraints (33), while "Without" does not. ACO=ant colony optimization, NN2=K-nearest-neighbor search with K=2, and BFS=brute-force search. Italicized values are estimates for cases that could not reach an optimum in the alloted time.

It was first observed that ACO runs extremely quickly in that it required <0.6 sec for all cases. Computation times for the other methods, however, varied over a wide range. To this point, NN2 gave computation times <10 msec for eight cases having 12 lymph nodes, while BFS gave computation times <10 msec for four cases having 8 lymph nodes (staging zone constraints used in all cases). Unfortunately, these two methods gave exponentially increasing times as the number of nodes increased, as demonstrated by Table 3. As an anecdotal test, we ran BFS using staging zone constraints for 23-node case 20349-15 for 1 week without reaching a solution (estimated run time≈1.64E+10 msec=190 days) see Table 3. On the other hand, ACO and NN2 required only 249 msec and 904 msec, respectively, for this case.

| Case | N | ACO With Zones | ACO Without | NN2 With Zones | NN2 Without | BFS With Zones | BFS Without |
|---|---|---|---|---|---|---|---|
| 20349_3_24 | 8 | 99 | 218 | 1 | 1 | 1 | 6 |
| 20349_3_11 | 12 | 179 | 372 | 1 | 2 | 16 | 67,191 |
| 20349_3_7 | 14 | 126 | 131 | 1 | 12 | 46,382 | 1.23E+07 |
| 20349_3_13 | 17 | 170 | 258 | 5 | 107 | 5.28E+06 | 5.03E+10 |
| 20349_3_15 | 23 | 249 | 519 | 904 | 13,119 | 1.64E+10 | 3.66E+18 |
| 20349_3_27 | 25 | 214 | 426 | 3,895 | 55,821 | 2.54E+14 | 2.19E+21 |

Figure 3D:
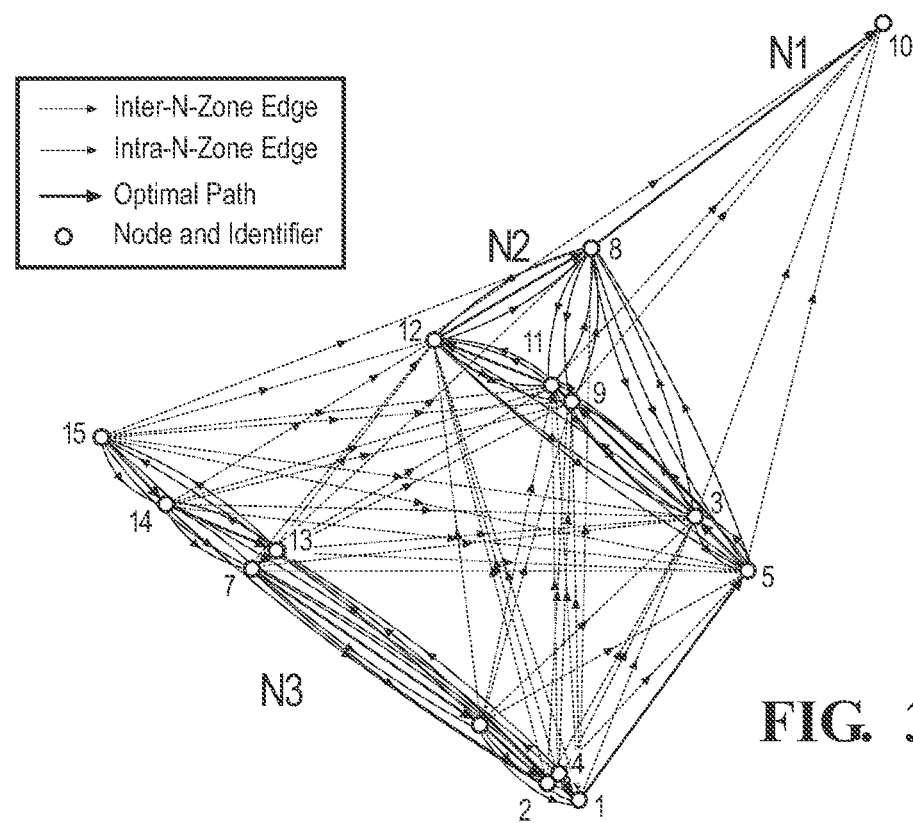
FIG. 3D shows a graph depicting the optimal tour (black arrows)

Also, as expected, the use of staging zone constraints breaks up a complex optimization problem into essentially three separate smaller optimization problems, as the graph of FIG. 3D illustrates. This tends to greatly lower the computation time, as Tables 2-3 exemplify. Nevertheless, the optimal brute-force search still demands a prohibitive effort for more complex patient cases. Along this line, if any one staging zone contains a large (>16) number of nodes, then the computation will become prohibitive. (We point out in passing that our database exhibits an imbalance in the number of nodes in each staging zone. Yet, this imbalance arises only because of the particular random selection of cases we consented. In reality, the nodes could be distributed over any zone with equal expectation.)

TABLE 4

Planning/Computation time in sec for the complete 3-step method for planning a comprehensive nodal staging procedure. The time for region definition, which entails user interaction, assumes 23 lymph nodes of interest. All other times are a mean over four patient cases.

| Operation | Time |
|---|---|
| 1. CT Preprocessing | 1983 |
| Region Definition | 1380 |
| Tree, routes, stations | 600 |
| IASLC nodal stations | 3 |
| 2. Staging Zones and Labeling | 1.05 |
| Graph construction | 0.01 |
| Staging zone construction | 0.41 |
| Node labeling | 0.64 |
| 3. ACO Tour Computation | 0.14 |

To put tour computation within the context of the present complete method for planning a comprehensive nodal staging bronchoscopy, we measured the total planning times for four patient cases (mean of 23 nodes per case; range, [13,31]). Table 4 gives a computation time breakdown for our three-step planning method.

All CT Preprocessing operations, except the computation of the nodal stations, are standard off-line operations for planning an image-guided bronchoscopy procedure [2, 24, 57, 69]. Hence, the computation time for these operations sets a baseline for the total planning time. Because these operations entail significant user interaction along with the analysis of a large 3D CT volume (typical size: 200 MB), the computation is substantial. Interactive region definition via the live wire is especially time-consuming and depends on the number of lymph nodes considered. Table 5 assumes 23 nodes/case and a time of 1 minute (60 sec) to define each node. In an effort to reduce this interaction time, recent methods for automatic lymph node identification could be applied [41].

Fortunately, the extra operations required to plan a comprehensive nodal staging procedure—namely, computations for the IASLC nodal stations, graph, staging zones, node labeling, and ACO tour computation—are fully automatic and require <6 sec total. By comparison, the standard CT Preprocessing operations take over ½ hour per case, accounting for >99% of the total planning time.

We next compared the tour lengths produced by the various tour computation methods. Note that, because of varying lung sizes and the number of nodes considered, tour lengths vary considerably from one patient to the next. Hence, for the 25 cases considered for the computation time tests, we calculated two tour lengths: the actual tour length L; and a relative tour length given by $$L_{rel} = ((L/L_{opt}) - 1) \times 100 \qquad (35)$$

where L is length of a tour found by an optimization method and $L_{opt}$ is the optimal (minimum) tour length [32]. Because the true $L_{opt}$ can only be found by a brute-force search—a prohibitively complex search for many cases as seen earlier, we estimated $L_{opt}$ for each case by running ACO (the best non-BFS algorithm) 50 separate trials and using the minimum length from these trials as $L_{opt}$. Regarding (35), $L_{rel}=0$ implies a derived tour that is 0% longer than the optimal tour, implying that the tour is almost certainly the optimum, while $L_{rel}=50$ implies a derived tour that is 50% longer than $L_{opt}$.

Tables 5 summarizes the tour length results. We first observe that absolute tour lengths varied considerably over the 25 test cases, as expected, from 105 mm to 562 mm. Hence, these results offer limited insight. Yet, ACO gave a tour length mean that was closest to the optimal brute-force search. More insightful are the results for $L_{rel}$. ACO gave a near optimal $L_{rel}=1.4\%$ and 1.9% with and without staging zone constraints, respectively, with the tour having maximum (worst) $L_{rel}$ having a tour length only 9.1% longer than its corresponding $L_{opt}$. Also, ACO gave the optimal tour for 13 of the 16 cases where the true optimum was known, while NN1 found an optimum in 2/16 cases, NN2 in 5/16, and greedy in 0/16. Clearly, both nearest-neighbor algorithms performed poorly when staging constraints were used, making them unreliable for staging procedures. Interestingly, the greedy approach, which represents the approach often applied by physicians for nodal staging, gave exceedingly long tours averaging 1.5 to 2.5 times longer than the optimal tour. By taking the approach of biopsying the largest nodes first, the physician generally must backtrack multiple times between the two lungs to complete a procedure.

TABLE 5

Summary of derived tour lengths over 25 test cases. The "Length" column summarizes the tour length measurements in mm, while the "Relative Length" column use the metric (35). "With Zones" indicates that staging zone constraints were used, while "Without" implies they were not. Since BFS gives the optimal results, all of its $L_{rel}$ values equal 0.

|  |  | Length L | | Relative Length $L_{rel}$ | |
|---|---|---|---|---|---|
|  |  | Mean ± std | Range | Mean ± Std | Range |
| With | ACO | 401 ± 171 | [105, 650] | 1.4 ± 1.0 | [0, 3.6] |
| Zones | NN1 | 608 ± 294 | [105, 1277] | 55.6 ± 33.4 | [0, 134] |
|  | NN2 | 502 ± 235 | [105, 943] | 31.0 ± 21.2 | [0, 72.7] |
|  | BFS | 352 ± 169 | [105, 562] | 0 ± 0 | [0, 0] |
|  | Greedy | 1004 ± 528 | [159, 1802] | 148 ± 83.4 | [26.9, 403] |
| Without | ACO | 304 ± 128 | [105, 519] | 1.9 ± 1.8 | [0, 9.1] |
|  | NN1 | 319 ± 141 | [105, 530] | 9.6 ± 6.2 | [0, 19.6] |
|  | NN2 | 305 ± 135 | [105, 519] | 5.7 ± 4.2 | [0, 15.6] |
|  | BPS | 220 ± 104 | [105, 372] | 0 ± 0 | [0, 0] |
|  | Greedy | 1115 ± 623 | [117, 2084] | 258 ± 140 | [11.7, 662] |

As expected, the derived tours are generally shorter when no staging zone constraints are used. Yet, for 3 cases having as many as N=12 nodes, the optimal tours were identical, with and without the constraints. This situation could easily happen for cases with few nodes (e.g., N<4), but such cases would not entail true comprehensive staging bronchoscopies, which by definition require visiting many nodes and nodal stations spanning the chest. Finally, the staging zone constraints are, of course, required for comprehensive staging. But important practical applications exist for using the present method without these constraints, as highlighted in Section 4.

5. Guidance Strategy and Software Implementation

Figure 4:
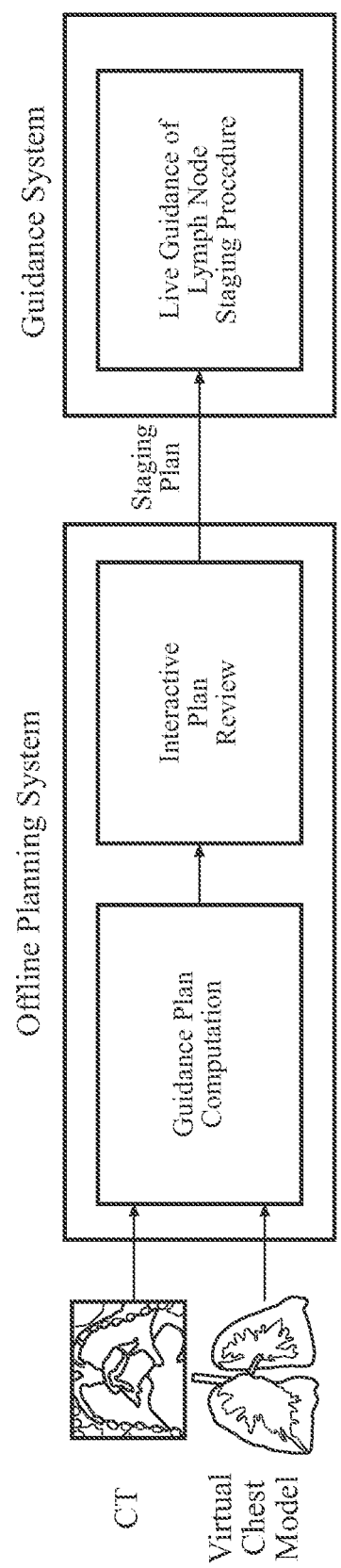
FIG. 4 shows a top-level lay-out and work flow of the software system.

A planning and image-guided bronchoscopy system is tailored to comprehensive nodal staging that draws on the present planning method. All software was coded in Microsoft Visual C++ using Visual Studio 2015 and utilizing several external software libraries including VTK, Qt, and OpenCV. We ran all tests on a custom-built Windows 10 64-bit computer (one 16-core 3.2 GHz AMD Threadripper 1950x CPU, 64 GB RAM) with an NVIDIA GTX 1080 Ti GPU. To begin, the complete system follows a two-part work flow, as illustrated in FIG. 4:

1. An off-line planning system, which creates a procedure plan, based on the previously described planning method, prior to the staging bronchoscopy.
2. An image-guided bronchoscopy (IGB) system used during the live nodal staging procedure to guide the physician along the preplanned tour of the patient's relevant lymph nodes.

Figure 5:
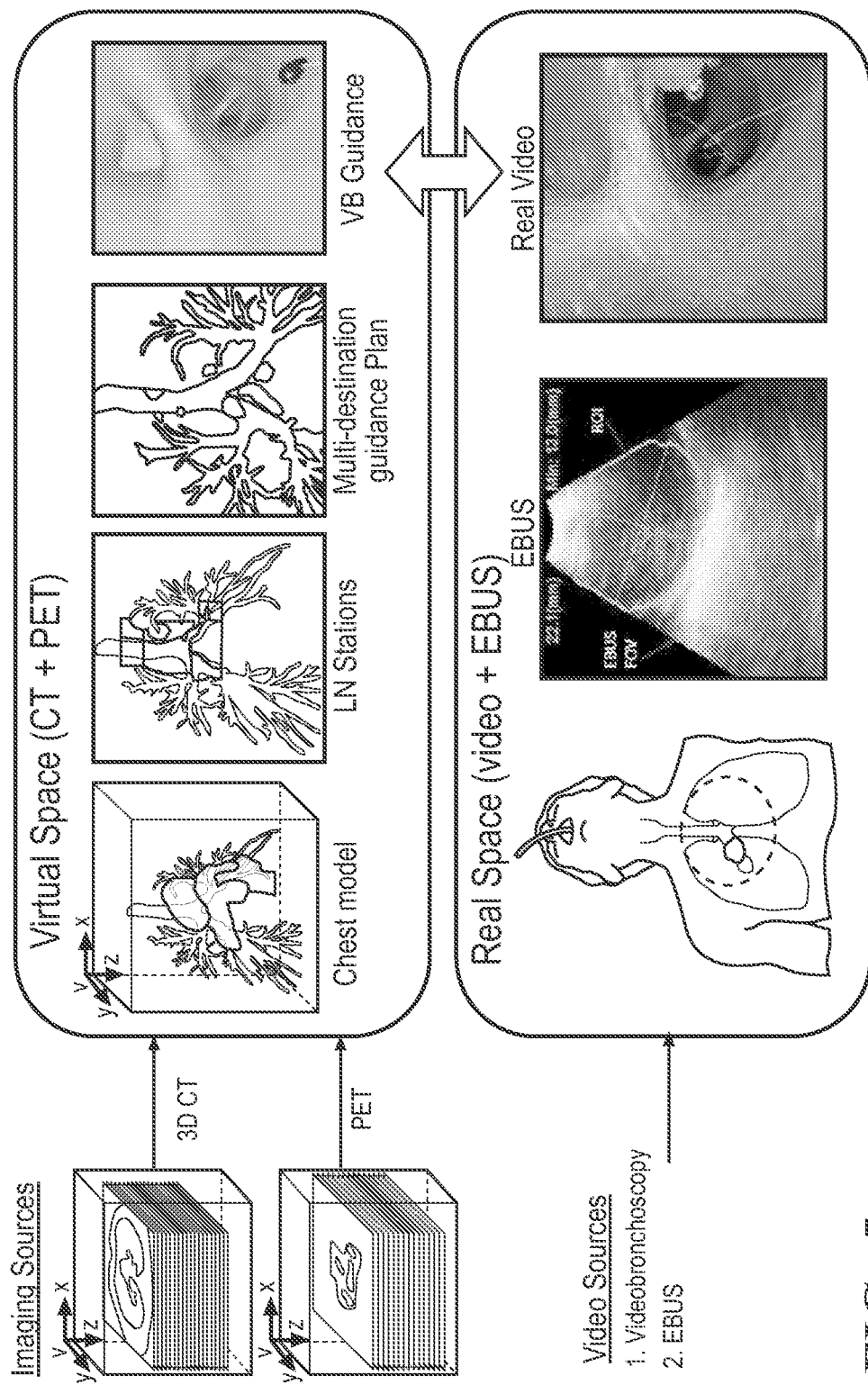
FIG. 5 shows a data flow diagram for the two-stage multi-destination lung cancer staging process; (The top row represents the virtual space derived from the patient's preoperative PET/CT data, while the bottom row denotes the real space, including the bronchoscopic video and possible endobronchial ultrasound (EBUS) produced during the procedure. During procedure planning, the system creates a tour of the designated lymph nodes and desired diagnostic sites. During live bronchoscopy, the guidance system provides image-based guidance for comprehensive nodal staging)

This two-component system is built around a 2-space environment used to link the planning data, derived in 3D virtual chest space, to the real space of the live procedure (FIG. 5). Within the 3D CT-based virtual chest space reside the patient's CT scan, PET scan, if available, chest model, and procedure plan. Within the real space are the bronchoscopy hardware's live videobronchoscopy stream and EBUS if available. The primary mechanism linking the two spaces and enabling image guidance are CT-based virtual bronchoscopy (VB) views (also known as endoluminal views) and the live bronchoscope's video views of the airway tree interior. As is well known, VB (endoluminal) views strongly resemble the appearance of the live videobronchoscopy views [48].

Figure 6:
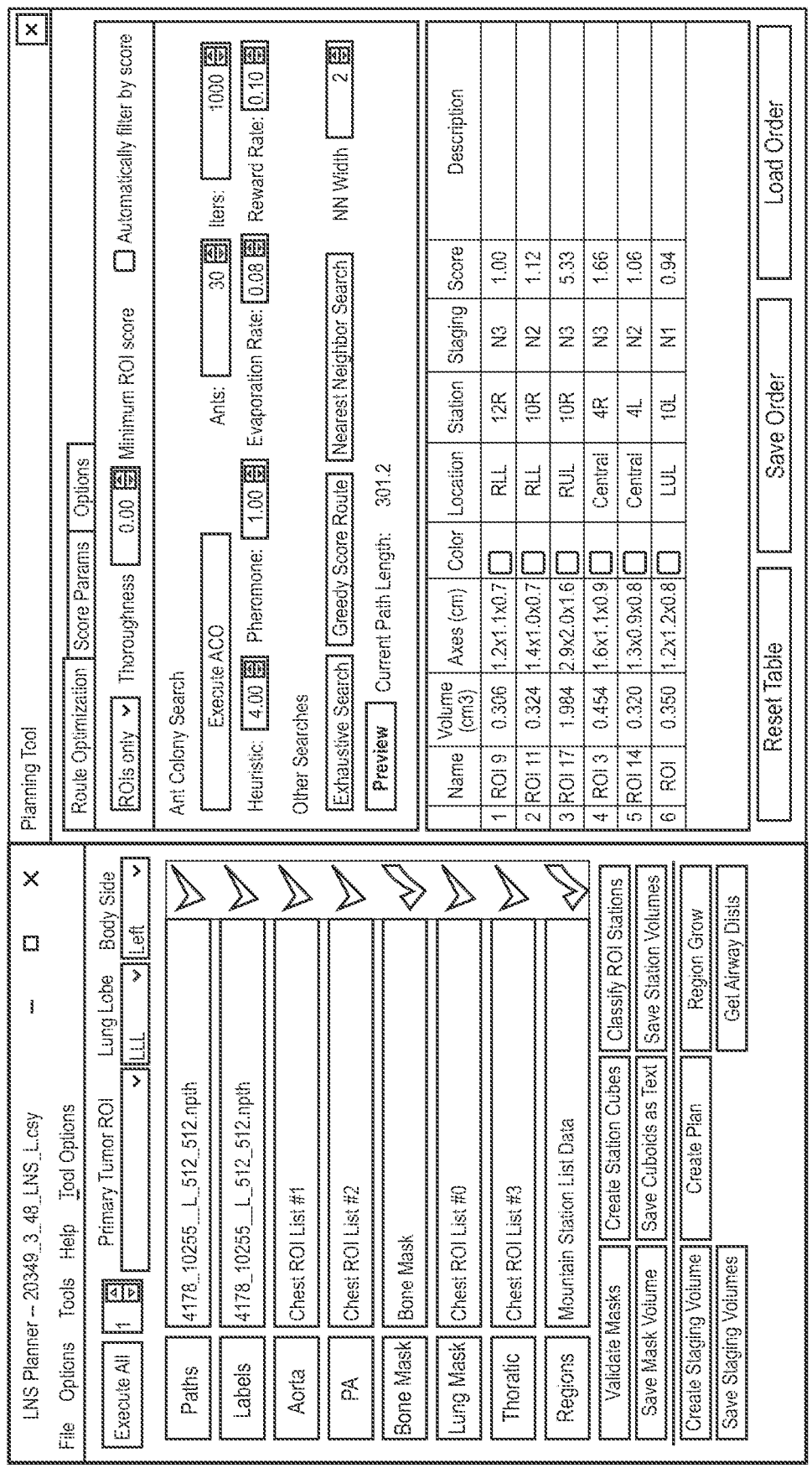
FIG. 6 shows a graphical user interface (GUI) for the procedure planning subsystem; (The left figure shows the loaded patient study with the CT-based chest model components loaded. It also gives a means for specifying the primary tumor (top right) and lists the operations run to execute the 3-step planning process (bottom). The right figure depicts how to compute the tour through the specified lymph nodes)

To begin, the planning subsystem, referred to as the LNS Planner (LNS=Lymph Node Staging), allows the physician to rapidly define the desired tour over a series of specified lymph nodes $n_t$, as shown in FIG. 6. For the example depicted in the figure, a tour of length 301.2 mm visiting six lymph nodes was generated using the ACO method. It also illustrates the automatically assigned station labels and staging zones assigned to the nodes.

Figure 7A:
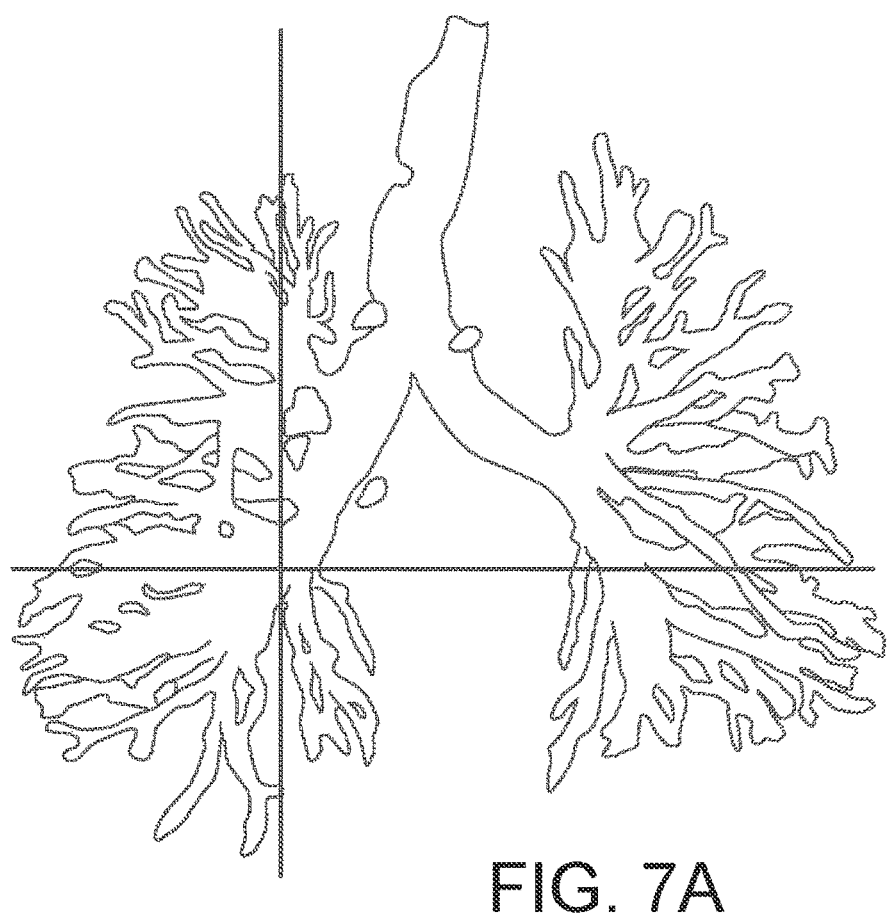
FIG. 7A shows LNS Planner facilities for visualizing generated lymph node tours.
Figure 7B:
FIG. 7B shows that the physician can play an endoluminal movie through the airway tree to see how the nodes are visited along the tour.

After computing the tour, the physician can use the LNS Planner's visual tools to interactively review the generated tour, as shown in FIGS. 7A and 7B. The user can view the tour dynamically along the 3D airway tree or within the airway tree's endoluminal surfaces.

Next, during bronchoscopy, we provide a system for live guidance that draws upon the previously computed multi-destination tour. The system acquires live endoscopic video as an input and provides virtual guidance along the pre-planned tour. The on-line guidance system also provides interactive plan review, live procedure guidance to multiple bronchoscopic targets, and enables comprehensive multi-destination lymph node staging procedures adhering to clinical best-practice guidelines.

Figure 8:
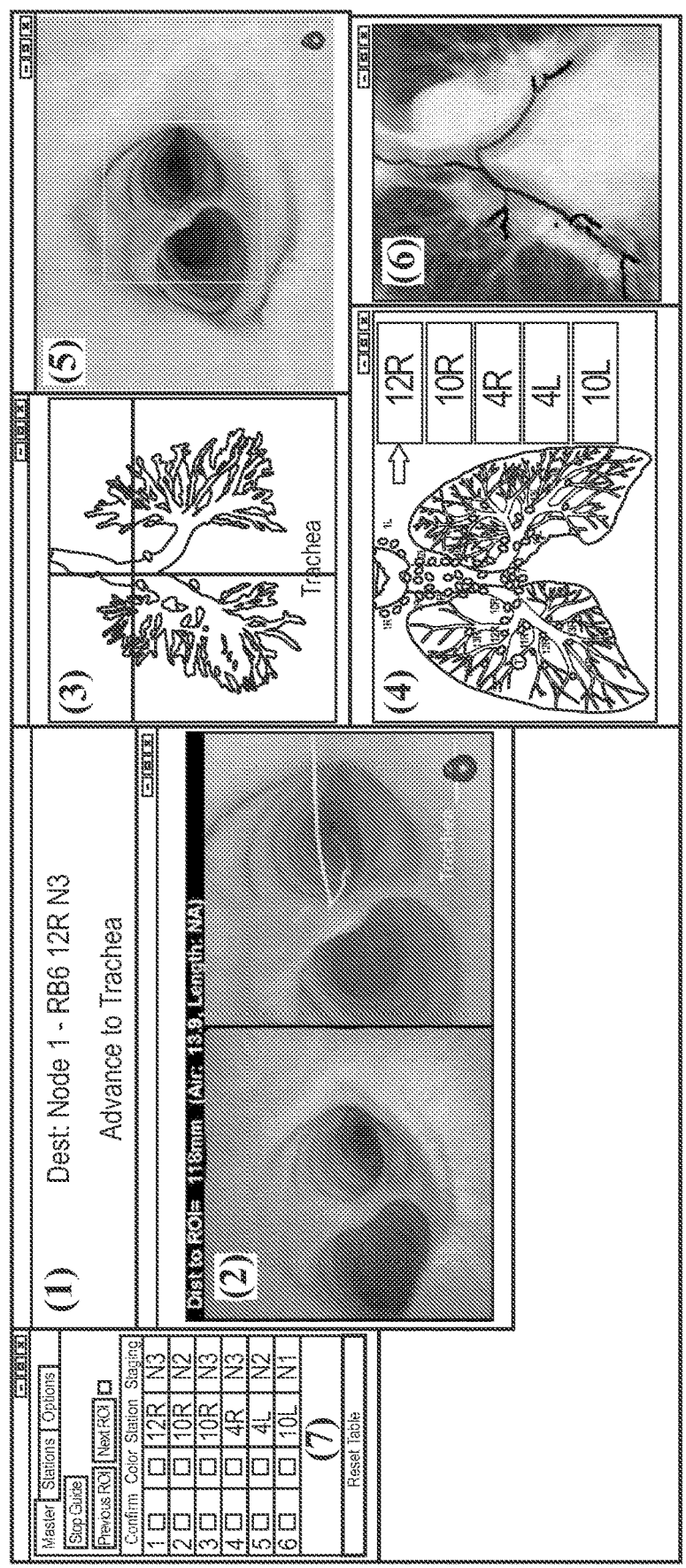
FIG. 8 shows a GUI for the image-guided system tailored to guiding a physician along a multi-destination tour of anatomical ROIs through the airway tree.

During the live procedure, the system display presents a series of tools to assist with guidance, shown in FIG. 8. These tools include:

1. Instruction Box (FIG. 8—center): Presents written directions during the procedure. The top row of text indicates the node destination information, namely the current node number, ROI location, IASLC station, and N-stage descriptor. The second row indicates the next suggested bronchoscope maneuver—this updates after every guidance movement.
2. CT-Video Match tool (FIG. 8—middle left): The primary visual tool considered during guidance. The left side depicts the live endoscopic video feed, while the right view depicts a system-generated VB view for the next guidance location. The tool unifies the real video and virtual space in one interface, allowing for ready review of the real and virtual bronchoscope poses. Furthermore, it can register the virtual space to the real bronchoscopic video, as shown in the figure [48].
3. Station Map tool (FIG. 8—lower left): Presents a static map of the IASLC lymph node stations and a live updating tracking interface, which displays which stations have had all nodes completed in the staging procedure. The right-side checklist provides an easy-to-grasp procedure progress tracker for completed nodes and stations. Yellow check marks indicate a partially complete multi-node station and a colored box with a green check mark denote completed stations. The static map shows the lymph node stations and uses a small black circle with a T to indicate the lung lobe of the primary tumor.
4. 3D Airway Tree Renderer (FIG. 8—top center right): This view gives a global look at the current guidance system location. It depicts the 3D airway tree, airway centerlines, guidance system position via cross hairs, and the current guidance route using a blue line.
5. Procedure Order tool (FIG. 8—top left): As the centralized control interface of the guidance system, the tool provides a detailed list of each ROI's station, staging zone, and color, while updating the guidance instructions for the physician. The tool starts and stops the multi-destination guidance mode and can move the system to station-specific endoluminal views.
6. Virtual Panorama (FIG. 8—top far right): A wide-angle view of the endoluminal renderer, this view expands the VB view displayed by the CT-Video match tool to enable visualization of ROIs that may not be visible when the scope is withdrawing.
7. Coronal Projection tool (FIG. 8—bottom far right): An x-ray-like view of the chest with overlaid airway centerlines, which provide live tracking of the system progress along the tour. Similar to the 3D airway tree view, this visualization provides visual context for the current guidance location and for an active ROI's final destination along the tour.

The CT-Video Match tool, Instruction Box, Station Map, and 3D Airway Tree Renderer form the system's primary guidance backbone, enabling the physician to determine the state of the bronchoscope in both the virtual guidance space and real surgical space simultaneously while tracking the progress of the procedure.

The Station Map gives a history of the progress along the tour through the chest. This is extremely useful and reassuring to the physician, as it gives indications of progress made during the procedure, the last ROI visited, and the nodal stations remaining to visit.

The other tools help inform the physician of their current location and assist in deciding how to make a suggested guidance maneuver. All previously computed ROI planning and labeling information transfers into the guidance system.

The maneuvers, provided in the Instruction Box, are computed automatically. The following maneuvers could be suggested:
1. Advance: Move the bronchoscope deeper into the lungs to the indicated airway position. The guidance system dynamically plays the suggested motion and ends at the next bifurcation.
2. Withdraw: Pull the scope back to a more proximal airway branch in the tree. This maneuver is used when going from a deeper ROI to either a shallower airway (e.g., trachea, right upper lobe (RUL) bronchus). The virtual maneuver animation smoothly pulls the virtual scope back to the least common ancestor bifurcation/branch in one motion.
3. Localize and Sample: This is the final instruction for reaching the current ROT. It is used when the system has reached the terminal guidance pose, and directs the physician to localize and sample the lymph node as needed.

Figure 9:
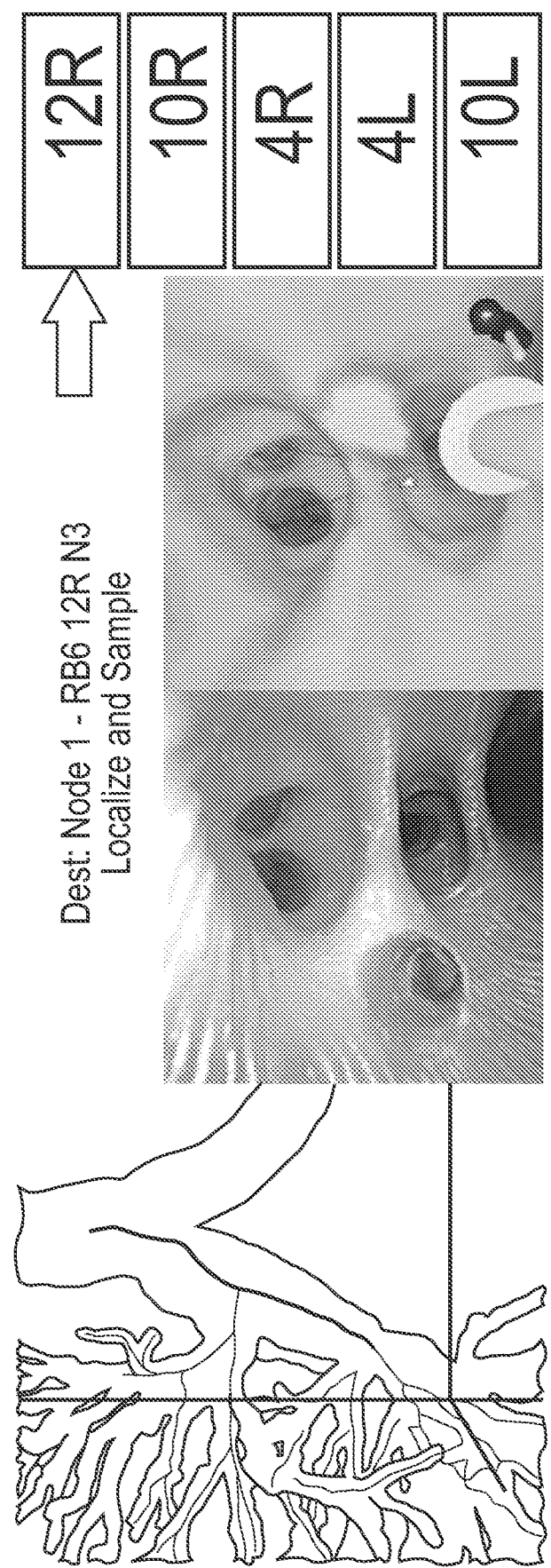
FIG. 9 shows a display for a few guidance tools upon reaching the destination for node 1 along the tour shown in FIG. 8.

For multi-destination guidance, navigation begins in the trachea for node 1, as shown in FIG. 8, and guides the physician sequentially from ROI to the next along the tour. All tools stay synchronized to the guidance system's global position, as guidance proceeds. After reaching the destination of a particular ROI, the system invokes several actions: 1) it displays a bright green display indicating the optimal sampling location for the current node, 2) it gives a "Localize and Sample" instruction, and 3) it indicates by an arrow on the Station Map the site just completed and all stations completed to date. FIG. 9 gives an example of the system reaching node 1.

Figure 10A:
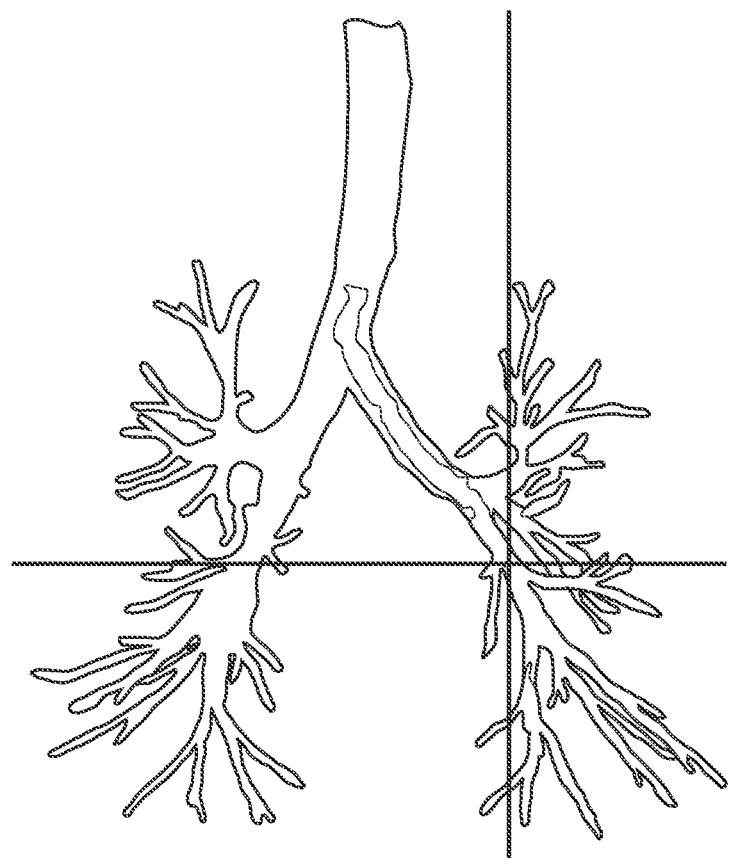
FIG. 10 shows a view of the image-guided bronchoscopy system after a physician reaches a station 12L lymph node located in the left lower lobe bronchus for patient 20349-3a; (The 3D Airway Tree view and Station Progress Map indicate the physician's location within the chest with red cross-hairs and an open disk, respectively. The CT-Video Tool shows the live videobronchoscopy frame [left] and corresponding VB view [right]; the VB view's green region indicates the 12L node)
Figure 10B:
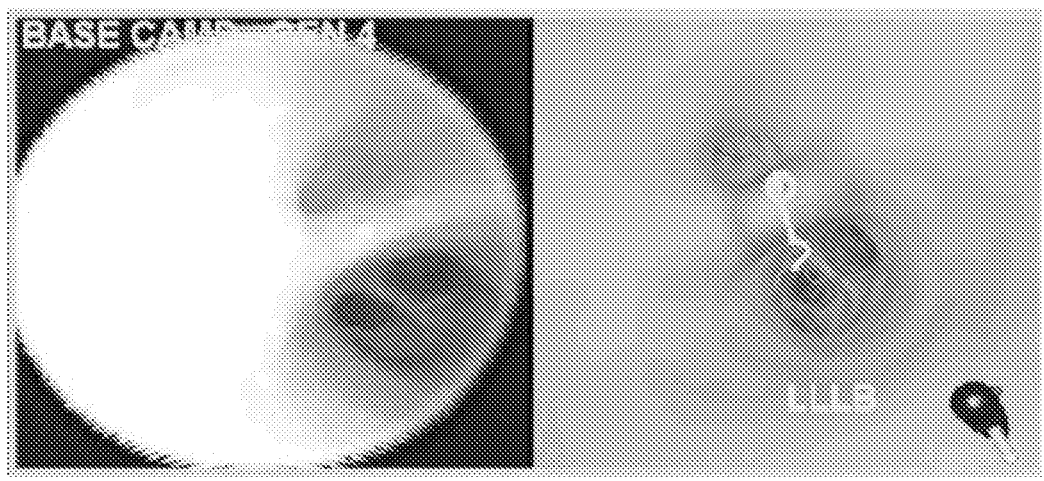
Figure 10C:
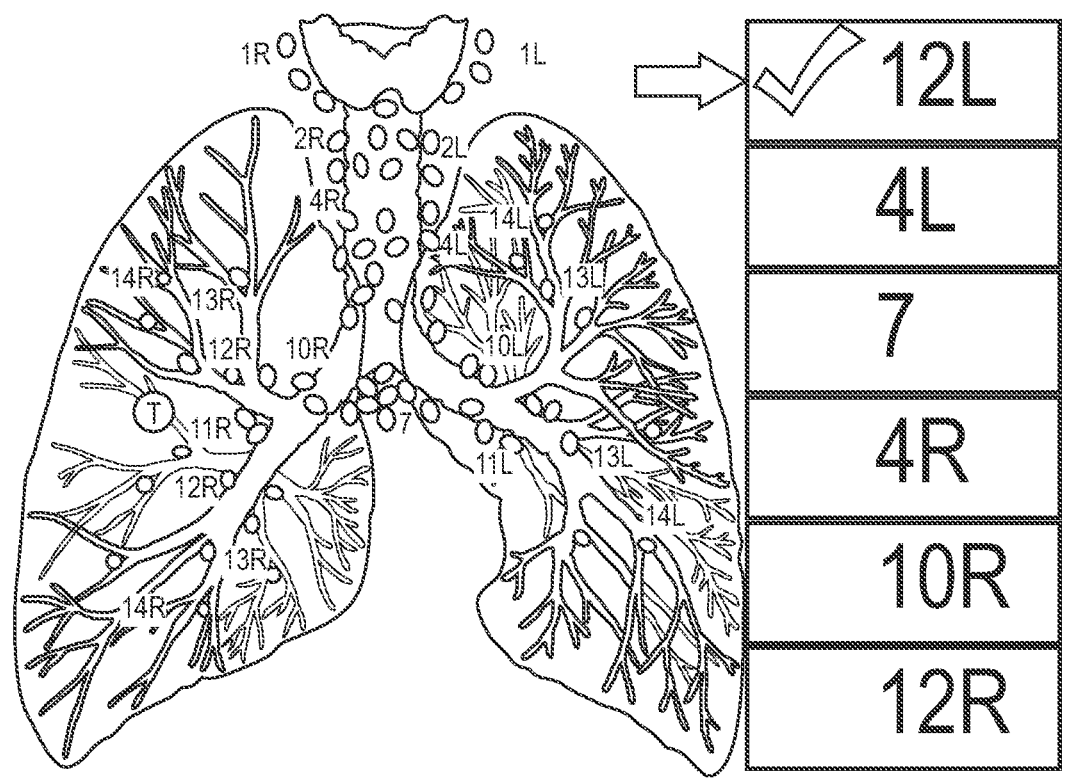

As a second composite guidance system example, FIG. 10 illustrates an application of the system for patient case 21405-3a with a right-side tumor. As shown by the Station Progress Map, the physician is tasked to locate nodes in IASLC stations 12L, 4R, 4L, 7, 10R, and 12R. For the composite system views shown, the physician has just confirmed reaching the first left-side node located in station 12L in the generation-4 LLLB (left lower lobe bronchus). The 3D Airway Tree view depicts the physician's current location with red cross-hairs. The CT-Video tool shows a matching live videobronchoscopy view and corresponding CT-based VB view, which indicates the node with the bright green region. Finally, the Station Progress Map gives the physician's approximate airway location on the lung map and also checks the box for station 12L, which confirms that all preplanned station 12L nodes have been examined.

Figure 11:
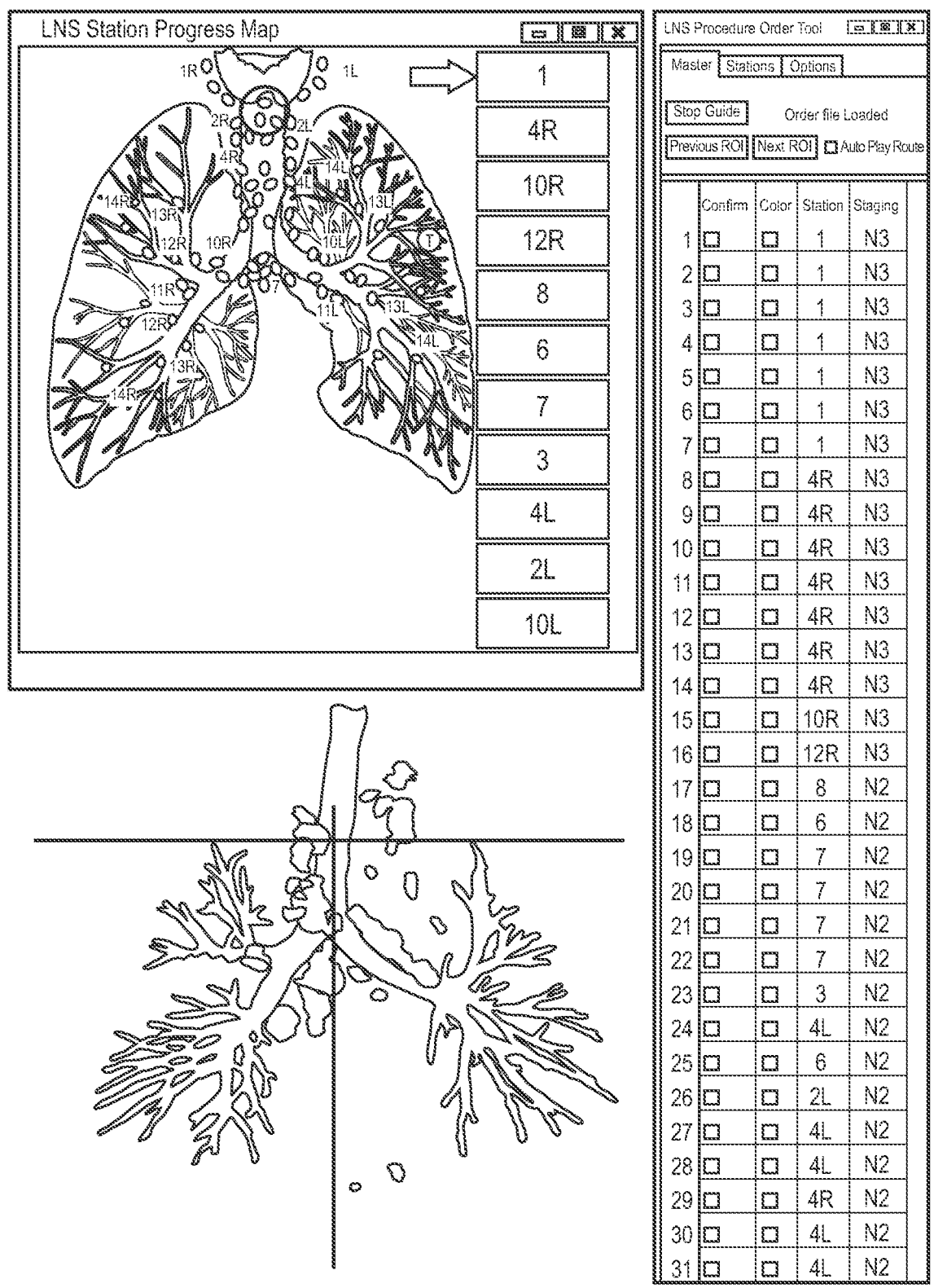
FIG. 11 shows sample guidance system views for patient 20349-13, having 38 lymph nodes spanning the range of IASLC nodal stations.

Next, FIG. 11 illustrates a few sample system views for a patient having 38 chest lymph nodes spanning the broad range of IASLC nodal stations. This tour was computed in under 1 sec using the present approach, but would be impossible to derive with other existing planning methods. Such situations are common for truly comprehensive lymph node staging. Also, procedures of similar complexity arise in other domains.

Using the planning and guidance methodology, we have completed tests with the two-part image-guided system involving retrospective human cases, controlled live animal experiments, a multi-physician guidance study, and an ongoing prospective human study [36].

As a natural extension that can prove very useful for endoscopic procedure planning, we also have a method for finding canonical view poses $p_c$ for reaching landmark locations within branching structures, such as the airway tree. The method easily extends to defining such views inside the endoluminal interiors of other branching anatomical structures such as the colon or the vasculature within the brain or liver.

For the airway tree, we created a rule-based decision tree method to locate the canonical station poses $p_c$ within the airway tree. Given a labeled airway tree and a priori knowledge of the IASLC lymph node station specifications, the method moves the virtual camera to a location that approximates a given IASLC nodal station. The airway labels and nodal stations are those already derived by the LNS Planner system from a patient's CT scan. A desired view pose is defined by a 3D position within the airway tree and a series of directions (pitch, roll, yaw, and up vector) that define the 3D viewpoint to position the endoscope. The algorithm to find this information is as follows:
1. Identify the trachea as branch 1 and the current branch $b_m$.
2. Jump to the last viewing site $v_{end}$ in $b_m$.
3. Identify the child branches of $b_m$: $b_a$ and $b_b$.
4. Following the defined knowledge specifying each station, label the children $b_a$ and $b_b$.
5. Define the station view by moving back to the viewing site that is at 80% of the branch length $0.8 \cdot b_i$ to provide a pose $p_c$ giving a suitable endoluminal view of the station.
6. Repeat from Step 2, setting $b_m$ to each of $b_a$ and $b_b$ in turn, until all poses are derived.

This method easily derives canonical nodal station views for the various IASLC nodal stations. FIGS. 12A-12I gives example canonical view poses derived for 3 example stations, while FIG. 13 illustrates the facility in our software for automatically deriving these poses for several nodal stations and airway tree locations; others are also possible.

The method easily extends to define similar view poses for the main branch points in the airway tree, often used as landmarks for patient airway examination. These landmarks include the main carina, left- and right-main bronchi, and the segmental airway bifurcations. In general. these view poses can serve as additional "general" diagnostic sites to enable orderly examination of tissue regions delineating, for example, a nodal station, an airway wall location, the location of a diffuse or ground glass nodule, or lobar/segmental tissue region. They are especially useful when it is difficult to define specific suspect sites, such as lymph nodes or tumors.

Figures 13, 14:
FIG. 13 shows a guidance system tool for generating sample canonical station and airway tree canonical pose views.
FIG. 14 shows a procedure history tool in the guidance system.

Lastly, the guidance system has a facility for saving a detailed procedure history, as the live procedure progress, as can be seen in FIG. 14. As a procedure progresses, complete state information pertaining to all performed device maneuvers, all guidance display views, all precise locations visited within the device's travel space (e.g., the airways when performing bronchoscopy), and all ROI imaging characteristics (e.g., CT data, volume, etc.) is recorded and saved. For our tool, the history can be reloaded for procedure review after the fact. The physician would invoke our guidance system, with its full complement of graphical viewers as discussed earlier, to recreate and study the procedure. In addition, procedure endoscopic video can be linked to the procedure. Standard playback controls exist, such as fast forward, rewind, etc. It is especially useful for examining specific ROI sites considered during a procedure.

This information has several valuable uses:
1. The physician can recreate the complete procedure using the guidance system, with the ability to focus on specific sites. In this way, the physician can complete a detailed review to assess procedure outcome and plan follow-on procedures, if necessary.
2. The data can be used in follow-up procedures. This enables assessment of treatment and/or disease progress at previously examined sites. Also, sites can be compared live during follow-up procedures, with it being possible to re-enact an an entire previous procedure live during a follow-up procedure.
3. The facility could be useful for monitoring drug/treatment delivery and testing over time.
4. The genesis of lung tumors, as they appear in chest CT and or PET imaging, could be monitored over time.

Applications, such as those listed above, are especially important for managing lung cancer patients, who generally must be followed up over time for many years. Similar issues also arise for monitoring cardiac patients and colon cancer patients.

In summary, because of the lack of adequate tools, physicians have no organized way of planning a complex multi-site endoscopic surgical procedure within a branching hollow network organ system. In addition, no related mechanism exists to guide the physician through the organ system during the procedure. Finally, tools for effective follow-up procedures also do not exist. As a result, physicians either performed inadequate simplified procedures involving only a few sites or don't perform the procedure at all.

To solve the problem, the present methods and system implementations help for planning and guiding a complex multi-site endoscopic surgical procedure within a branching hollow network organ system. As demonstrated for the task of lung cancer staging, the present method helps planning a comprehensive nodal staging bronchoscopy. Results with human CT data show that the method gives optimal or near-optimal tours through the lungs in under a few seconds, regardless of the number of nodes selected. This compares favorably to other methods, which either give unacceptable tours or are unable to provide a tour in a practical time. In addition, the present method incorporates IASLC nodal station labels and staging zone constraints to give a procedure plan abiding by state-of-the-art clinical staging guidelines.

The planning method is incorporated into an image-guided bronchoscopy system tailored to staging bronchoscopy. Laboratory, animal, and human studies indicate that the system has considerable potential for enabling efficient comprehensive nodal staging, regardless of physician experience/skill level [36].

With the present methods, a physician could perform more complex multi-site procedures they heretofore would not or could not perform. With the efficiency offered by the present methods and the intuitive cues provided by our guidance strategy, the physician could perform a complex procedure with less stress, work more quickly, and complete a task more accurately. The guidance aids offer a means to be more thorough, with less potential confusion on the completeness of a procedure. Finally, the path history capability offers a means to review complex procedures and better plan future follow-up procedures. Overall, the present method enables more accurate and complete outcomes for the patient.

A major long-term value of the present methods will be in the burgeoning domain of robotics-driven bronchoscopy [18, 67]. An automated robotic device could also follow the directions and quantitative information of the guidance strategy. In addition, the robotics system could draw on the guidance system's visualization aids to enable a human operator to monitor the robot's progress. Using a robotics system, it could become feasible to perform an exhaustive staging procedure involving >20 lymph nodes, a procedure likely to be too tedious for a human to complete. While we have focused on staging bronchoscopy, our methods could be applied to other multi-destination tasks, if no staging-zone constraints are used. Examples of pulmonary applications are: 1) guidance of multimodal airway exams for the detection of early mucosal cancer lesions along the airway walls [61]; 2) guidance to multiple airway sites for asthma or cancer treatment delivery; and 3) coordination of airway exams performed over repeat follow-up visits, with the purpose of monitoring developing or recurring lung disease. The present methods could also be applicable to other organ domains involving complex branching structures, such as the lung or renal vasculature.

REFERENCES

[1] Fumihiro Asano, Ralf Eberhardt, and Felix J F Herth. Virtual bronchoscopic navigation for peripheral pulmonary lesions. *Respiration,* 88(5):430-440, November 2014.

[2] F. Asano. Practical application of virtual bronchoscopic navigation. In A. Mehta and P. Jain, editors, *Interventional Bronchoscopy*, volume 10 of *Respir. Med.*, pages 121-140. Humana Press, 2013.

[3] J. Bentley. Fast algorithms for geometric traveling salesman problems. *ORSA J. Comput.,* 4(4):387-411, 1992.

[4] Christopher Burrows, Fangde Liu, Alexander Leibinger, Riccardo Secoli, and Ferdinando Rodriguez y Baena. Multi-target planar needle steering with a bio-inspired needle design. In Giovanni Boschetti and Alessandro Gasparetto, editors, *Advances in Italian Mechanism Science*, pages 51-60, 2017.

[5] Sharad Chandrika and Lonny Yarmus. Recent developments in advanced diagnostic bronchoscopy. *European Respiratory Review,* 29(157):1-11, September 2020.

[6] Gerard J Criner, Ralf Eberhardt, Sebastian Fernandez-Bussy, Momen M Wahidi, et al. Interventional bronchoscopy: State-of-the-art review. *Am. J. Respir. Crit. Care Med.,* (1):29-50, July 2020.

[7] G. A. Croes. A method for solving traveling-salesman problems. *Oper. Research,* 6(6):791-812.

[8] Frank C Detterbeck, Daniel J Boffa, Anthony W Kim, and Lynn T Tanoue. The eighth edition lung cancer stage classification. *Chest,* 151(1):193-203, January 2017.

[9] Frank Detterbeck, Jonathan Puchalski, Ami Rubinowitz, and David Cheng. Classification of the thoroughness of mediastinal staging of lung cancer. *Chest*, 137(2):436-442, February 2010.

[10] M. Y. Dolina, D. C. Cornish, S. A. Merritt, L. Rai, R. Mahraj, W. E. Higgins, and R. Bascom. Interbronchoscopist variability in endobronchial path selection: a simulation study. *Chest*, 133(4):897-905, April 2008.

[11] Marco Dorigo, Mauro Birattari, and Thomas Stutzle. Ant colony optimization. *IEEE Comput. Intell. Mag.*, 1(4):28-39, November 2006.

[12] Marco Dorigo and Luca Maria Gambardella. Ant colonies for the travelling salesman problem. *Biosystems*, 43(2):73-81, July 1997.

[13] Marco Dorigo, Vittorio Maniezzo, and Alberto Colorni. Ant system: optimization by a colony of cooperating agents. *IEEE Trans. Sys., Man, Cyber., Pt. B*, 26(1):29-41, February 1996.

[14] M. Dorigo and L. M. Gambardella. Ant colony system: a cooperative learning approach to the traveling salesman problem. *IEEE Trans. Evol. Comput.*, 1(1):53-66, April 1997.

[15] A. H. El-Sherief, C. T. Lau, C. C. Wu, R. L. Drake, G. F. Abbott, and T. W. Rice. International association for the study of lung cancer (IASLC) lymph node map: radiologic review with CT illustration. *Radiographics*, 34(6):1680-1691, October 2014.

[16] A. Ernst, G. A. Silvestri, and D. Johnstone. Interventional pulmonary procedures: guidelines from the American College of Chest Physicians. *Chest*, 123(5):1693-1717, May 2003.

[17] John L. Falcone, Xiaotian Chen, and Giselle G. Hamad. The traveling salesman problem in surgery: economy of motion for the FLS peg transfer task. *Surg. Endosc.*, 27(5):1636-1641, May 2013.

[18] David Fielding and Masahide Oki. Technologies for targeting the peripheral pulmonary nodule including robotics. *Respirol.*, 25:914-923, September 2020.

[19] James H Finigan and Jeffrey A Kern. Lung cancer screening: past, present and future. *Clin. Chest Med.*, 34(3):365-371, September 2013.

[20] Erik Folch, Daniel B Costa, Jeffrey Wright, and Paul A VanderLaan. Lung cancer diagnosis and staging in the minimally invasive age with increasing demands for tissue analysis. *Transl. Lung Cancer Res.*, 4(4):392-403, August 2015.

[21] Erik Folch and Adnan Majid. Point: are >50 supervised procedures required to develop competency in performing endobronchial ultrasound-guided transbronchial needle aspiration for mediastinal staging?Yes. *Chest*, 143(4):888-891, April 2013.

[22] Michael R. Garey and David S. Johnson. *Computers and Intractability: A Guide to the Theory of NP-Completeness*. W.H. Freeman, San Francisco, 1979.

[23] R. Gayle, P. Segars, M. C. Lin, and D. Manocha. Path planning for deformable robots in complex environments. *Robotics: Science and Systems*, pages 225-232, June 2005.

[24] J. D. Gibbs, M. W. Graham, R. Bascom, D. C. Cornish, R. Khare, and W. E. Higgins. Optimal procedure planning and guidance system for peripheral bronchoscopy. *IEEE Trans. Biomed. Engin.*, 61(3):638-657, March 2014.

[25] J. D. Gibbs, M. W. Graham, and W. E. Higgins. 3D MDCT-based system for planning peripheral bronchoscopic procedures. *Comp. Biol. Med.*, 39(3):266-279, March 2009.

[26] Peter Goldstraw, Kari Chansky, John Crowley, Ramon Rami-Porta, et al. The IASLC lung cancer staging project: proposals for revision of the TNM stage groupings in the forthcoming (eighth) edition of the TNM classification for lung cancer. *J. Thor. Oncol.*, 11(1):39-51, January 2016.

[27] B. E. Goyette and C. N. Riviere. Reducing operating time of a crawling robot for epicardial surgery. In *Proc. 2010 IEEE 36th Ann. Northeast Bioeng. Conf.*, pages 1-2, 2010.

[28] M. W. Graham, J. D. Gibbs, D. C. Cornish, and W. E. Higgins. Robust 3D Airway-Tree Segmentation for Image-Guided Peripheral Bronchoscopy. *IEEE Trans. Medical Imaging*, 29(4):982-997, April 2010.

[29] Gaël Guennebaud, Benoit Jacob, et al. Eigen. URl: http://eigen. tuxfamily. org, 3, 2010.

[30] W. E. Higgins, T. Kuhlengel, and R. Bascom. Automated 3D CT-Based lymph node station definition for the IASLC 8th edition guidelines. *Am. J. Respir. Crit. Care Med.*, 201:A4447, May 2020.

[31] Karla L Hoffman, Manfred Padberg, and Giovanni Rinaldi. Traveling salesman problem. In *Encyclopedia of operations research and management science*, pages 1573-1578. Springer, 2013.

[32] David S Johnson and Lyle A McGeoch. The traveling salesman problem: A case study in local optimization. In E. H. L. Aarts and J. K. Lenstra, editors, *Local Search in Combinatorial Optimization*, pages 215-310. John Wiley & Sons, 1997.

[33] R. Khare, R. Bascom, and W. E. Higgins. Hands-free system for bronchoscopy planning and guidance. *IEEE Trans. Biomed. Eng.*, 62(12):2794-2811, December 2015.

[34] C Matthew Kinsey and Douglas A Arenberg. Endobronchial ultrasound-guided transbronchial needle aspiration for non-small cell lung cancer staging. *Am. J. Resp. Crit. Care Med.*, 189(6):640-649, March 2014.

[35] Trevor K. Kuhlengel and William E. Higgins. Bronchoscopic procedure planning for systematic lymph node analysis. In *Med. Imag.: Image-Guided Proc., Robotic Interven., and Modeling*, volume 10951, page 1095110. International Society for Optics and Photonics.

[36] T. Kuhlengel. *Planning and Guidance of Bronchoscopy for Comprehensive Lymph Node Staging*. PhD thesis, The Pennsylvania State University, Department of Computer Science and Engineering, 2022.

[37] Vijay Kunadian, Alaide Chieffo, Paolo G Camici, Colin Berry, Javier Escaned, Angela HEM Maas, Eva Prescott, Nicole Karam, Yolande Appelman, Chiara Fraccaro, et al. An EAPCI expert consensus document on ischaemia with non-obstructive coronary arteries in collaboration with european society of cardiology working group on coronary pathophysiology and microcirculation endorsed by coronary vasomotor disorders international study group. *Europ. Heart J.*, 41(37):3504-3520, 2020.

[38] Didier Lardinois, Paul De Leyn, Paul Van Schil, Ramon Rami Porta, et al. ESTS guidelines for intraoperative lymph node staging in non-small cell lung cancer. *Eur. J. Cardio-thoracic Surg.*, 30(5):787-792, 2006.

[39] P. Larrañaga, C. M. H. Kuijpers, R. H. Murga, I. Inza, and S. Dizdarevic. Genetic algorithms for the travelling salesman problem: A review of representations and operators. *Artif Intell. Rev.*, 13(2):129-170, 1999.

[40] S. Lin and B. W. Kernighan. An effective heuristic algorithm for the traveling-salesman problem. 21(2):498-516, 1973.

[41] Jiamin Liu, Joanne Hoffman, Ronald M Summers, et al. Mediastinal lymph node detection and station mapping on chest CT using spatial priors and random forest. *Med. Phys.*, 43(7):4362-4374, July 2016.

[42] Xiongbiao Luo and Kensaku Mori. Real-time bronchoscope three-dimensional motion estimation using multiple sensor-driven alignment of CT images and electromagnetic measurements. *Comp. Med. Imaging Graphics*, 38(6):540-548, September 2014.

[43] K. Lu, P. Taeprasartsit, R. Bascom, R. P. M. Mahraj, and W. E. Higgins. Automatic definition of the central-chest lymph-node stations. *Int. J. Computer Assisted Radiol. Surgery*, 6(4):539-555, 2011.

[44] K. Lu, P. Taeprasartsit, R. Bascom, R. P. M. Mahraj, and W. E. Higgins. Automatic definition of the central-chest lymph-node stations. *Int. J. Computer Assisted Radiol. Surgery*, 6(4):539-555, 2011.

[45] J. F. Aguilar Madeira, H. L. Pina, E. B. Pires, and J. Monteiro. Surgical correction of scoliosis: Numerical analysis and optimization of the procedure. *Int. J. Numer. Meth. Biomed. Eng.*, 26(9):1087-1098, September 2010.

[46] Makoto Matsumoto and Takuji Nishimura. Mersenne twister: a 623-dimensionally equidistributed uniform pseudo-random number generator. *ACM Transactions on Modeling and Computer Simulation*, 8(1):3-30, January 1998.

[47] S. A. Merritt, J. D. Gibbs, K. C. Yu, V. Patel, L. Rai, D. C. Cornish, R. Bascom, and W. E. Higgins. Image-guided bronchoscopy for peripheral lung lesions: A phantom study. *Chest*, 134(5):1017-1026, November 2008.

[48] S. A. Merritt, R. Khare, R. Bascom, and W. E. Higgins. Interactive CT-video registration for image-guided bronchoscopy. *IEEE Trans. Med. Imaging* 32(8):1376-1396.

[49] Russell J Miller, Lakshmi Mudambi, Macarena R Vial, Mike Hernandez, and George A Eapen. Evaluation of appropriate mediastinal staging among endobronchial ultrasound bronchoscopists. *Ann. Am. Thorac. Soc.*, 14(7):1162-1168, July 2017.

[50] H. Minami, Y. Ando, F. Nomura, S. Sakai, and K. Shimokata. Interbronchoscopist variability in the diagnosis of lung cancer by flexible bronchoscopy. *Chest*, 105(2):1658-1662, June 1994.

[51] D. P. Naidich and T. J. Harkin. Airways and lung: correlation of CT with fiberoptic bronchoscopy. *Radiol.*, 197(1):1-12, October 1995.

[52] National Lung Screening Trial Research Team. Results of initial low-dose computed tomographic screening for lung cancer. *New Engl. J. Med.*, 368(21):1980-1991, 23 May 2013.

[53] Carl A Nelson, David J Miller, and Dmitry Oleynikov. Modeling surgical tool selection patterns as a "traveling salesman problem" for optimizing a modular surgical tool system. *Stud. Health Technol. Inform.*, 132:322-326, 2008.

[54] David E Ost, Armin Ernst, Xiudong Lei, David Feller-Kopman, et al. Diagnostic yield of endobronchial ultrasound-guided transbronchial needle aspiration: results of the AQuIRE bronchoscopy registry. *Chest*, 140(6):1557-1566, December 2011.

[55] S. Y. Park, D. Sargent, I. Spofford, K. G. Vosburgh, et al. A colon video analysis framework for polyp detection. *IEEE Trans. Biomed. Eng.*, 59(5):1408-1418, May 2012.

[56] Ramón Rami-Porta, Sergi Call, Christophe Dooms, Carme Obiols, Marcelo Sinchez, William D Travis, and Ivan Vollmer. Lung cancer staging: a concise update. *Eur Respir J*, 51(5):1-17, May 2018.

[57] P. J. Reynisson, H. O. Leira, T. N. Hernes, E. F. Hofstad, et al. Navigated bronchoscopy: a technical review. *J. Bronchology Interv. Pulmonol.*, 21(3):242-264, July 2014.

[58] AM Reynolds. Chemotaxis can provide biological organisms with good solutions to the travelling salesman problem. *Phys. Rev. E*, 83(5):052901-1-052901-4, May 2011.

[59] D. Rosenkrantz, R. Stearns, and P. Lewis. An analysis of several heuristics for the traveling salesman problem. *SIAM J. Comput.*, 6(3):563-581, 1977.

[60] Valerie W Rusch, Hisao Asamura, Peter Goldstraw, et al. The IASLC lung cancer staging project: a proposal for a new international lymph node map in the forthcoming seventh edition of the TNM classification for lung cancer. *J. Thor. Oncol.*, 4(5):568-577, April 2009.

[61] Alejandro H Sardi and Shaheen Islam. Early lung cancer detection, mucosal, and alveolar imaging. *Curr. Opinion Pulm. Med.*, 22(3):271-280, May 2016.

[62] Rebecca L. Siegel, Kimberly D. Miller, and Ahmedin Jemal. Cancer statistics, 2020. *CA Cancer J. Clin.*, 70(1):7-30, January/February 2020.

[63] G. A. Silvestri, A. V. Gonzalez, M. A. Jantz, M. L. Margolis, et al. Methods for staging non-small cell lung cancer: Diagnosis and management of lung cancer, 3rd ed: American College of Chest Physicians evidence-based clinical practice guidelines. *Chest*, 143(5):e211S-e250S, May 2013.

[64] D. Sudholt and C. Thyssen. Running time analysis of ant colony optimization for shortest path problems. *J. Disc. Alg.*, 10(7):165-180, January 2012.

[65] Lynn T Tanoue, Nichole T Tanner, Michael K Gould, and Gerard A Silvestri. Lung cancer screening. *Am. J. Respir. Crit. Care Med.*, 191(1):19-33, 1 Jan. 2015

[66] Huai-Kuang Tsai, Jinn-Moon Yang, Yuan-Fang Tsai, and Cheng-Yan Kao. An evolutionary algorithm for large traveling salesman problems. *IEEE Trans. Syst. Man Cybern. Part B Cybern.*, 34(4):1718-1729, August 2004.

[67] M. M. Wahidi, F. J. F. Herth, A. Chen, G. Cheng, and L. Yarmus. State of the art: Interventional pulmonology. *Chest*, 157(3):724-736, March 2020.

[68] K. C. Yu, E. L. Ritman, and W. E. Higgins. System for the analysis and visualization of large 3D anatomical trees. *Comp. Biol. Med.*, 37(12):1802-1820, December 2007.

[69] Xiaonan Zang, Jason D. Gibbs, Ronnarit Cheirsilp, Patrick D. Byrnes, Jennifer Toth, Rebecca Bascom, and William E. Higgins. Optimal route planning for image-guided EBUS bronchoscopy. *Comp. in Biol. and Med.*, 112:103361, September 2019.

[70] Wen-Zhao Zhong, Si-Yang Liu, and Yi-Long Wu. Numbers or stations: From systematic sampling to individualized lymph node dissection in nonâ€"small-cell lung cancer. *J. Clin. Oncol.*, 35(11):1143-1145, April 2017.

[71] Y. Zhou. Runtime analysis of an ant colony optimization algorithm for TSP instances. *IEEE Trans. Evol. Comp.*, 13(5):1083-1092, October 2009.

The invention claimed is:

1. A method for planning a tour visiting a set of target diagnostic sites via endoscopy passing through a hollow organ system, said method comprising the steps of:
   receiving a 3D pre-operative imaging scan depicting the diagnostic sites and hollow organ system;
   receiving information on the target diagnostic sites in the 3D imaging scan;

computing a 3D virtual space of the hollow organ system from the 3D imaging scan;

computing a series of preliminary endoscopic routes leading to each diagnostic site, each preliminary endoscopic route consisting of a set of contiguous device poses through the hollow organ system that connect each target diagnostic site to all of the other target diagnostic sites, each pose consisting of its coordinates in the 3D virtual space and a set of vectors indicating a direction of travel through the hollow organ system;

defining a cost between each pair of diagnostic sites as the distance accumulated by the smallest set of contiguous poses connecting the pair of diagnostic sites together within the hollow organ system; and computing an optimal tour having a minimum cost corresponding to the smallest set of contiguous poses that visit all of the target diagnostic sites once and only once.

2. The method according to claim 1, wherein the step of computing the optimal tour comprises:

constructing a graph structure defined by a set of N vertexes, a set of edges and a cost matrix, each of the N vertices corresponding to one of the diagnostic sites, each of the N vertices having N−1 edges to the other N−1 vertices, the cost matrix having a plurality of entries, each entry of the cost matrix defined as a distance between two diagnostic sites; and computing a shortest tour corresponding to the minimum cost sequence of vertices that visits each and every vertex once and only once.

3. The method according to claim 1, wherein the 3D pre-operative imaging scan is a CT or MRI scan.

4. The method according to claim 1, wherein the hollow organ system includes lung airways, vasculature in a heart, brain, liver, kidney or hollow areas in a colon, stomach, bladder, pelvis/abdomen.

5. The method according to claim 1, wherein the endoscope is a bronchoscope, colonoscope, laparascope, angioscope, or cystoscope.

6. The method according to claim 1, wherein the diagnostic sites are lymph nodes, suspect lesions, or treatment delivery sites.

7. The method according to claim 1, further comprising defining disjoint nodal stations representing tissue regions in the 3D virtual space of a chest abiding by a predefined guideline.

8. The method according to claim 7, further comprising mapping the nodal stations into staging zones.

9. The method according to claim 8, further comprising incorporating constraints imposed by the staging zones while computing the optimal tour.

10. The method according to claim 7, wherein the predefined guideline is IASLC guidelines.

11. An image-guided endoscopy method used during a live medical procedure to guide an operator along a preplanned tour of the patient's target diagnostic sites at a hollow organ system, the method comprising:

devising the preplanned tour of the patient's target diagnostic sites according to the method of claim 1;

providing live videoendoscopy views within a real space of the live medical procedure;

linking planning data derived in the 3D virtual space to the real space of the live medical procedure and enabling image guidance based on virtual endoscopy endoluminal views and the live videoendoscope views of the hollow organ system;

providing suggested device maneuvers for reaching each diagnostic site;

indicating when a specific site has been reached during the live medical procedure; and tracking a procedure history indicating which sites have been visited and which sites are yet to be visited during the live medical procedure.

12. A system for continuous guidance of endoscopy during a live procedure along a preplanned tour of a hollow organ system of a patient to multiple target diagnostic sites, comprising:

an endoscope operative to navigate within the hollow organ system;

a display device operative to display live, real endoscopic (RE) images and live videoendoscopic views obtained by the endoscope;

a memory storing a precomputed planning data derived in a 3D virtual space constructed from 3D image data;

a processor in communication with the memory and display, the processor being operative to perform the steps of claim 11.

* * * * *